(12) United States Patent
Ahmed et al.

(10) Patent No.: US 11,147,870 B2
(45) Date of Patent: Oct. 19, 2021

(54) **SPECIFIC BINDING AGENTS TO VARICELLA-ZOSTER VIRUS AND USES RELATED THER

SPECIFIC BINDING AGENTS TO VARICELLA-ZOSTER VIRUS AND USES RELATED THERETO

CROSS-REFERENCE TO RELATED APPLICATIONS

This application claims the benefit of U.S. Provisional Application No. 62/662,335 filed on Apr. 25, 2018. The entirety of this application is hereby incorporated by reference for all purposes.

STATEMENT REGARDING FEDERALLY SPONSORED RESEARCH

This invention was made with government support under AI090023 awarded by the National Institutes of Health. The government has certain rights in this invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 18123US_ST25.txt. The text file is 15 KB, was created on Apr. 25, 2019, and is being submitted electronically via EFS-Web.

BACKGROUND

Infection by human herpesvirus 3, or varicella-zoster virus, causes chicken pox. Following this acute infection, the virus remains dormant in nerve ganglia for an individual's lifetime, and reactivation of the virus later in life manifests as shingles, a painful condition characterized by rash and blisters. While vaccines can prevent infection, or reduce the likelihood of shingles occurrence, treatment for shingles after it has developed is currently limited to antiviral medications to inhibit viral replication. The antiviral agents are not universally effective. Thus, there is a need to develop improved therapies.

Pregnant women that have not been previously infected with varicella-zoster virus are at an increased risk of complications if exposed to someone with an active infection. One treatment option involves the administration of varicella zoster immunoglobulins (VariZIG™). See Bapat et al., Expert Rev Vaccines, 2013, 12:1243-1248.

Orenstein et al. report prophylaxis of varicella in high-risk children using zoster immune globulin. J Pediatr, 1981, 98:368-373.

Birlea et al. report human anti-varicella-zoster virus (VZV) recombinant monoclonal antibody produced after Zostavax® immunization recognizes the gH/gL complex and neutralizes VZV infection. J Virol, 2013, 87(1):415-21.

Xing et al. report epitope mapping of neutralizing antibodies that bind residues on both glycoprotein H and glycoprotein L, thereby recognizing the gH/gL complex. Proc Natl Acad Sci USA, 2015, 112(19):6056-61.

Sullivan et al. report breadth and functionality of Varicella-Zoster virus glycoprotein-specific antibodies identified after Zostavax® vaccination in humans. J Virol. 2018, 92(14): e00269-18.

References cited herein are not an admission of prior art.

SUMMARY

This disclosure relates to specific binding agents to varicella-zoster virus proteins or glycoproteins. In certain embodiments the specific binding agents are antibodies and binding fragments thereof disclosed herein. In certain embodiments, this disclosure relates to methods of treating or preventing a varicella-zoster infection comprising administering an effective amount of a specific binding agent disclosed herein to a subject in need thereof. In certain embodiments, this disclosure relates to pharmaceutical compositions comprising specific binding agents disclosed herein and a pharmaceutically acceptable excipient.

In certain embodiments, this disclosure relates to recombinant chimeric antibodies, wherein the antibody comprises a heavy chain having a variable and constant region and a light chain having a variable and constant region. In certain embodiments, the antibody specifically binds glycoprotein H of varicella-zoster virus. In certain embodiments, the antibodies are non-naturally occurring chimeric antibodies.

In certain embodiments, a subject for treatment with specific binding agents disclosed herein is at high risk for complications due to exposure to an active varicella-zoster infection. In certain embodiments, the subject is immunocompromised, pregnant, newborn of mother with varicella shortly before or after delivery, premature infant, infant less than one year of age, or a subject without evidence of immunity.

In certain embodiments, this disclosure relates to specific binding agents, antibodies, or antigen binding fragments comprising complementarity determining region 3 (CDR3) of the heavy chain derived from an antibody selected from antibodies 301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and/or complementarity determining region 3 (CDR3) of the light chain derived from an antibody selected from antibodies 5301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and wherein the antibody or antigen binding fragment thereof specifically binds to an epitope expressed in an varicella-zoster virus glycoprotein.

In certain embodiments, this disclosure relates to specific binding agents, antibodies, or antigen binding fragments comprising complementarity determining regions, CDR2 and CDR3, of the heavy chain derived from an antibody selected from antibodies 301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and/or complementarity determining regions, CDR2 and CDR3, of the light chain derived from an antibody selected from antibodies 5301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and wherein the antibody or antigen binding fragment thereof specifically binds to an epitope expressed in an varicella-zoster virus glycoprotein.

In certain embodiments, this disclosure relates specific binding agents, antibodies, or antigen binding fragments comprising six complementarity determining regions (CDRs) or consensus sequences thereof, wherein the CDRs comprise the three heavy chain CDRs (CDR1, CDR2 and CDR3) derived from an antibody selected from antibodies 301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and/or wherein the CDRs comprise the three light chain CDRs (CDR1, CDR2 and CDR3) derived from an antibody selected from antibodies 5301-1G5, 302-1B12, 302-1C12, 302-1D11, 302-1G9, 303-1A8, 303-1A12, 303-1B2, 303-1C1, 303-1C2, 303-106, 303-1C9, 303-1D7, 303-1E3, 303-1E8, 303-1E12, MH259723/MH259748; 303-1F5, 303-1F7, 303-1G1, 304-1A12, RM-1A2, RM-1D1, RM-2D6, RM-5A2, and RM-5B3, and wherein the antibody or antigen binding fragment thereof specifically binds to an epitope expressed in an Varicella-Zoster virus glycoprotein.

In certain embodiments, the specific binding agents, antibodies, or antigen binding fragments comprise the three heavy chain CDRs of antibody RM-2D6 within SEQ ID NO: 7 EVQLVESGGGVVQPGRSLRLS-CAASGFMFSSYGMHWVRQAPGKGLEWVAAVS HDGTNDLYADSVKGRF SISRDNSKNTLYLQMNSL-RAEDTAVYYCAKTSWARFLEWTF DYWGQGTLVTVSS; CDR 1 (SEQ ID NO: 3) GFMFSSYG; CDR2 (SEQ ID NO: 4) VSHDGTND; and CDR3 (SEQ ID NO: 1) AKTSWARFLEWTFDY; and the three light chain CDRs of antibody RM-2D6 within SEQ ID NO: 8 DIQMTQSPSSLSASVGDRVTITCRASQSIN-RYLNWYQQKPGKAPKLLIYGASSLQSGVPL RFSGSGSGTDFTLTISSLQPEDFATYYCQQSH-STPTFGQGTRLEIK; CDR 1 (SEQ ID NO: 5) QSINRY; CDR 2 (SEQ ID NO: 6) GASS; and CDR 3 (SEQ ID NO: 2) QQSHSTPT.

In certain embodiments, the specific binding agents, antibodies, or antigen binding fragments comprise the three heavy chain CDRs of antibody 302-1G9 within SEQ ID NO: 15 QVQLVQSGAEVKKP-GASVKVSCEAFGYTFSNYGFTWVRQAPGQ-GLEWMGWIS ASNANTKYGQKFRGRVTLTTDTST-STAYMELRNLGYDDTAMYYCARDRGGSLAMVV GLDHWGQGTLVTVSS; CDR 1 (SEQ ID NO: 11) GYTFSNYG; CDR2 (SEQ ID NO: 12) ISASNANT; and CDR3 (SEQ ID NO: 9) ARDRGGSLAMVVGLDH; and the three light chain CDRs of antibody 302-1G9 within SEQ ID NO: 16 DIQMTQSPTSLSASVGDRVTIT-CRASQSIGGYLNWYQQNPGKAPKLLI-YAASTLQRGVPS RFSGGGSGTDFTLTITSLQPEDFA-TYYCQQCYSAELTFGGGTKVEIK; CDR 1 (SEQ ID NO: 13) QSIGGY; CDR 2 (SEQ ID NO: 14) AAST; and CDR 3 (SEQ ID NO: 10) QQCYSAELT.

In certain embodiments, the chimeric antibody comprises a Fc domain comprising the sequence LALA (SEQ ID NO: 138) and/or YTE.

In certain embodiments, the specific binding agents, antibodies, or antigen binding fragments are capable of neutralizing varicella-zoster virus infection of cells or preventing varicella-zoster virus from spreading between cells.

In certain embodiments, the disclosure relates to nucleic acids encoding specific binding agents, antibodies, or antigen binding fragments disclosed herein or a vector or expression system comprising such a nucleic acid. In certain embodiments, vectors comprising a nucleic acid are in operable combination with a heterologous promoter. In certain embodiments, the nucleic acid encodes the heavy and/or light chain of an antibody disclosed herein. In certain embodiments, the nucleic acid is a single nucleic acid or multiple nucleic acids encode protein individually. In certain embodiments, vectors contain a vector element or selectable marker.

In certain embodiments, the disclosure relates to pharmaceutical compositions comprising the specific binding agents, antibodies, or antigen binding fragments disclosed herein, and a physiologically acceptable carrier or excipient.

In certain embodiments, the disclosure relates to methods of preventing or treating a varicella-zoster virus infection comprising administering an effective amount of a pharmaceutical composition disclosed herein to a subject in need thereof. In certain embodiments, the subject is at risk of, exhibiting symptoms of, or diagnosed with a varicella-zoster virus infection.

In certain embodiments, this disclosure relates to methods of treating or preventing a varicella-zoster infection comprising administering an effective amount of a recombinant chimeric antibody disclosed herein to a subject in need thereof. In certain embodiments, the antibodies are non-naturally occurring chimeric antibodies. In certain embodiments the subject is at high risk of complications from an infection, immunocompromised, newborn of mother with varicella shortly before or after delivery, premature infant, infant less than one year of age, pregnant, or a subject without evidence of immunity.

DETAILED DESCRIPTION

Figure 1:
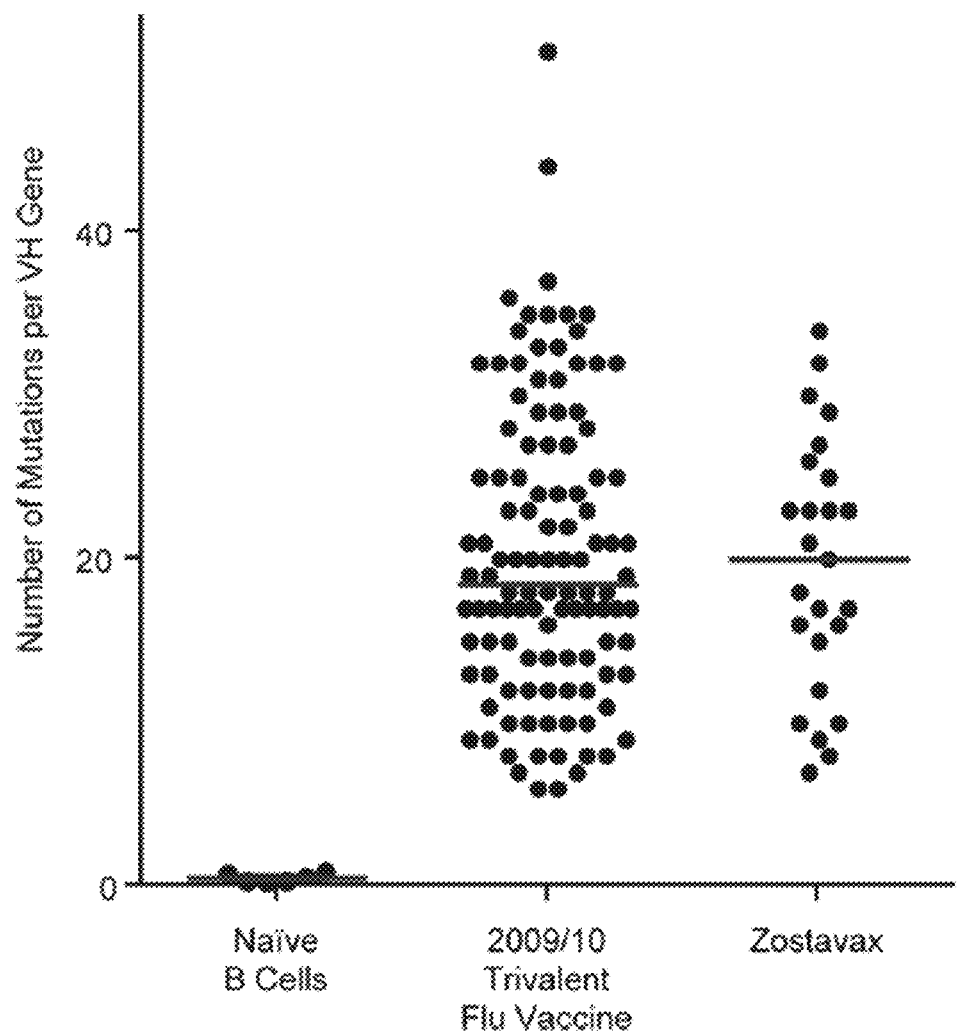
FIG. 1 compares the number of VH somatic hypermutations in naïve B cells, ASCs sorted from 2009/10 influenza trivalent vaccine and ZOSTAVAX® vaccinated ASCs. IG-BLAST was used to determine the number of somatic hypermutations (Fr1-CDR3 Heavy chain).
Figure 2:
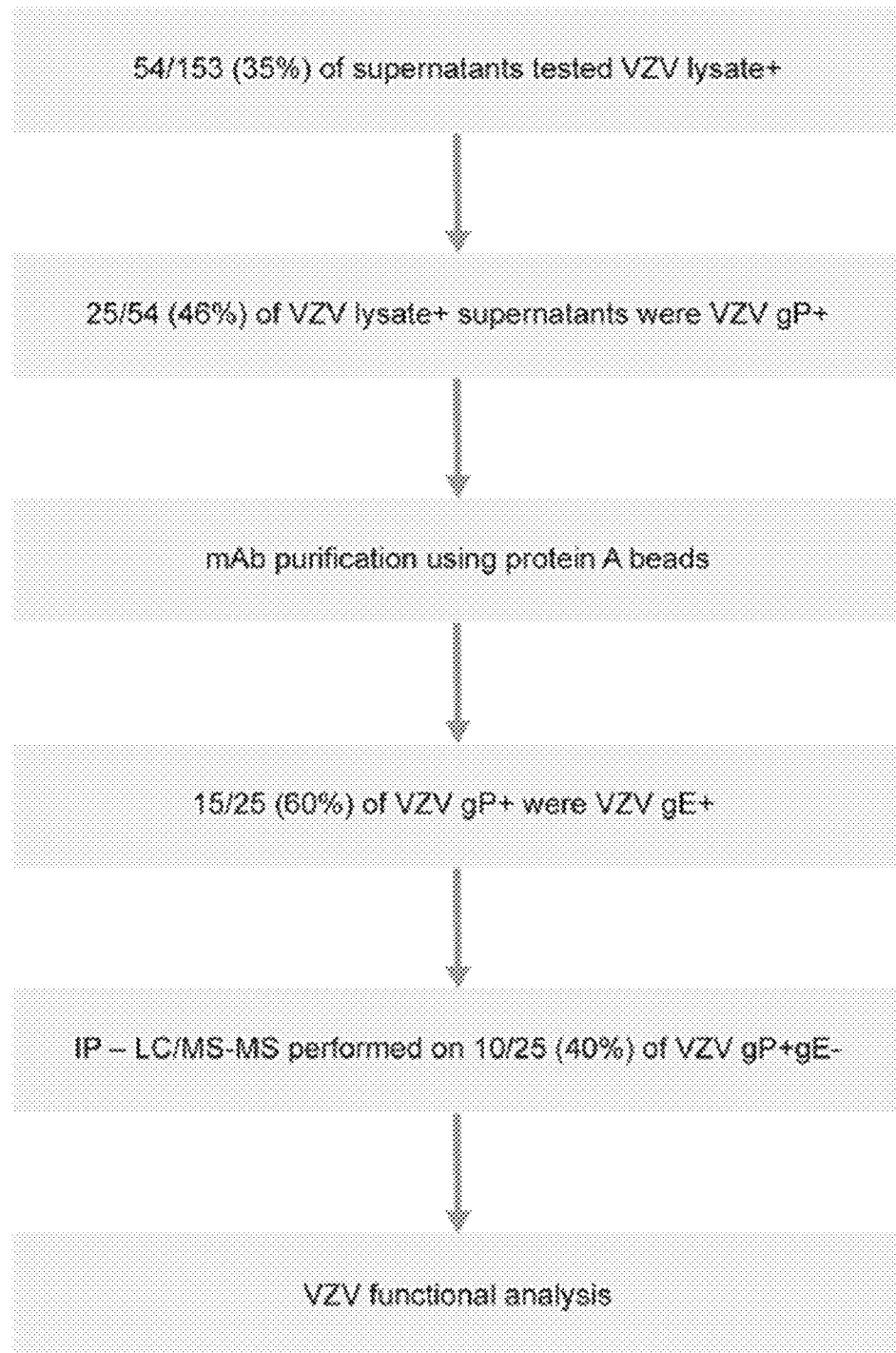
FIG. 2 describes work flow to identify glycoprotein-specific VZV monoclonal antibodies. Supernatant generated using ASCs single cell sorted, cloned and expressed in Expi293 cells were tested for VZV lysate binding via ELISA. VZV glycoprotein positive but non-gE antibodies (10/25) were tested via immunoprecipitation followed by LC/MS to determine the specificity. All glycoprotein positive antibodies were then tested for neutralization and cell-to-cell spread inhibition in vitro.
Figure 3:
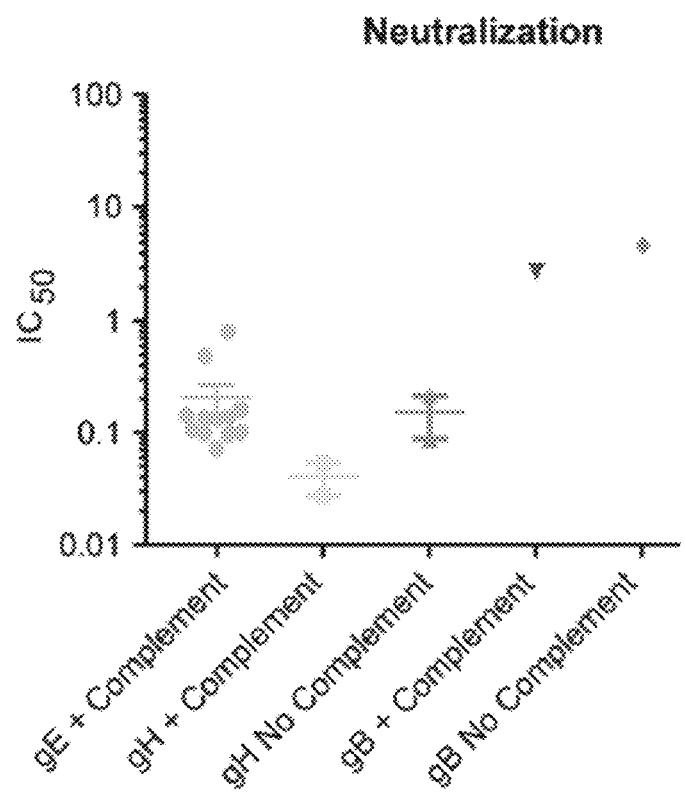
FIG. 3 shows data from neutralization plots with gH, gE and gI-specific monoclonal antibodies added.
Figure 4A:
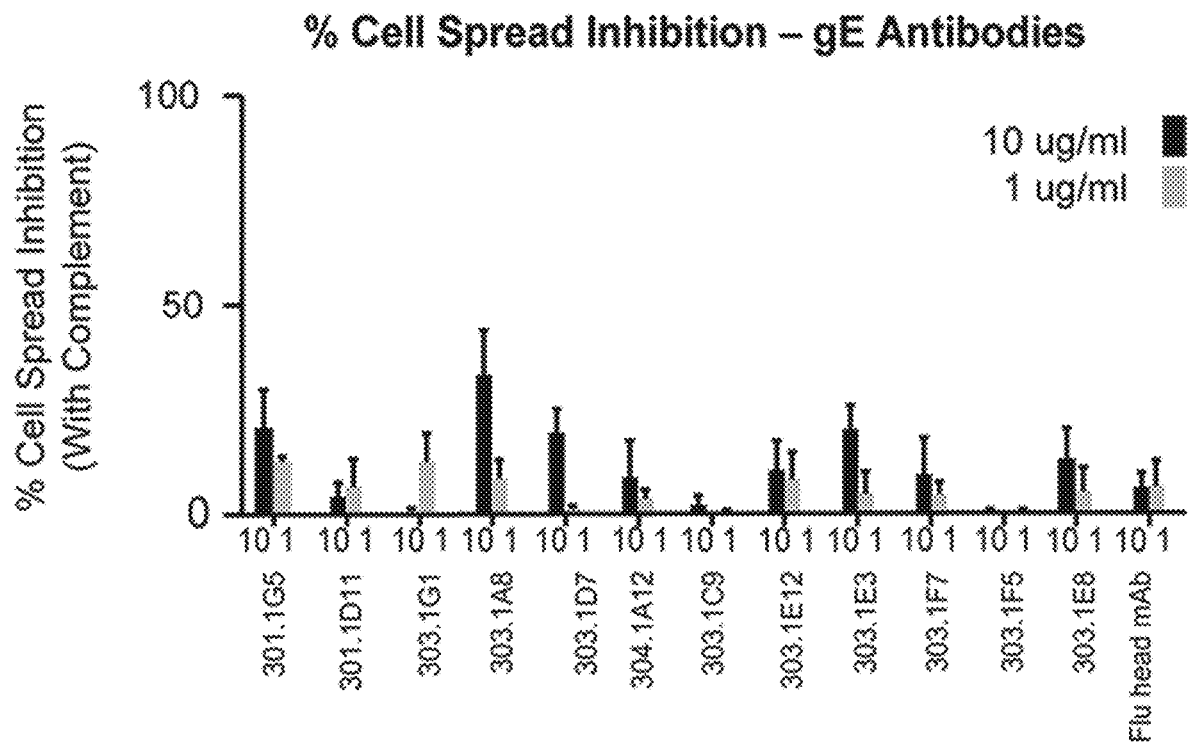
FIG. 4A shows data on in vitro inhibition of cell-to-cell spread by VZV. Cumulative data for anti-gE antibodies (top) and non-gE antibodies (bottom) are shown. Black bars represent antibodies added at 10 μg/ml and gray bars represent the same antibodies added at 1 μg/ml.
Figure 4A:
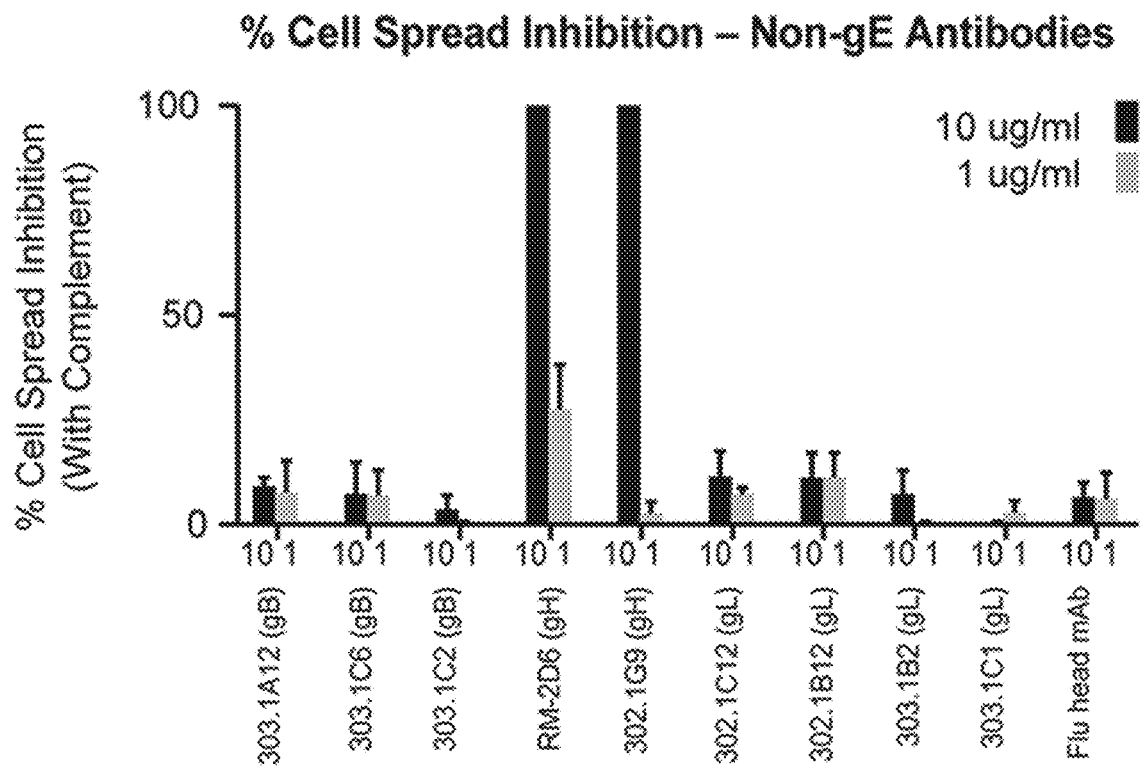
Figure 4B:
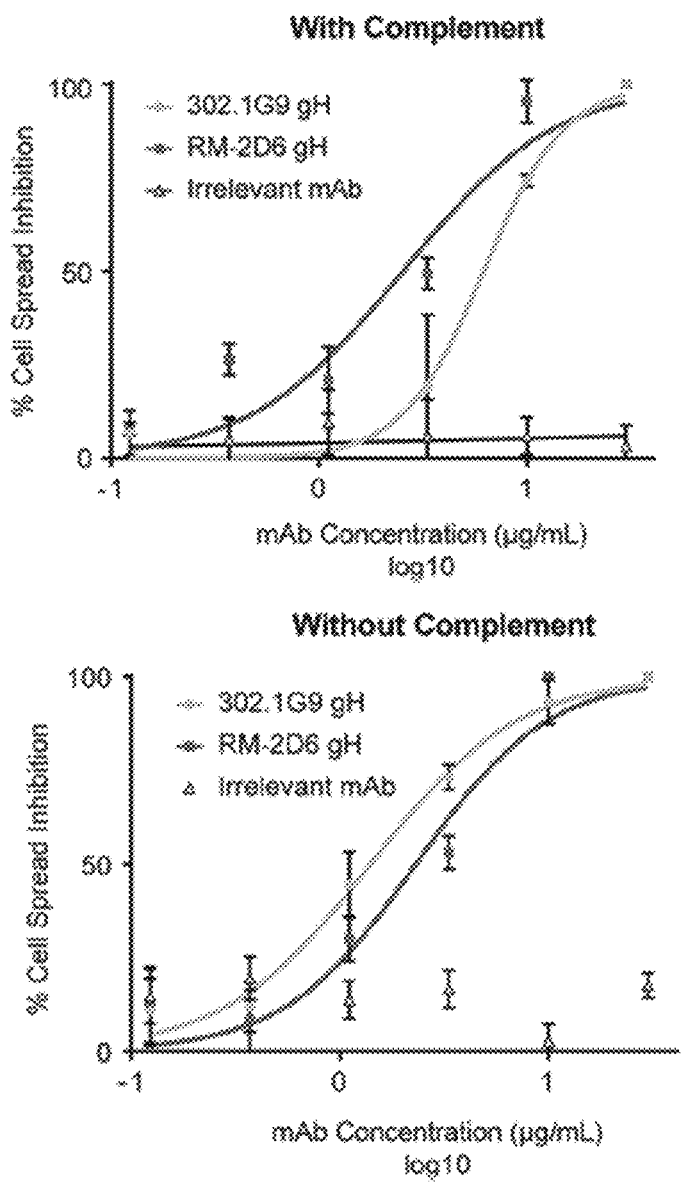
FIG. 4B shows cell-to-cell spread inhibition curves with $IC_{50}$ values (μg/ml) with anti-gH or irrelevant mAbs, with (top) or without (bottom) complement added.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

The term "epitope" as used herein refers to a molecular structure capable of being recognized by an antibody through binding or otherwise interacting. Epitopes may consist solely of amino acids, or contain a mixture of amino acids and sugars.

The term "monoclonal" as used herein refers to an antibody made from a single genetic source, such that all antibodies have the same amino acid composition and recognize the same epitope.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, Trends Biochem. Sci. 26:230; Nuttall et al., 2000, Cur. Pharm. Biotech. 1:253; Reichmann and Muyldermans, 1999, J. Immunol. Meth. 231:25; International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to the disclosed B7-H5 antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind an antigen. Such fragments include Fab', F(ab')2, Fv, single chain (ScFv), and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, non-naturally occurring chimeric or humanized derivatives of anti-VZV virus antibodies are particularly preferred for in vivo use in humans, however, murine antibodies or antibodies of other species may be advantageously employed for many uses (for example, in vitro or in situ detection assays, acute in vivo use, etc.). A humanized antibody may comprises amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a varicella-zoster virus polypeptide.

Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such that the entire molecule is not naturally occurring. Examples of chimeric antibodies include those having a variable region derived from a non-human antibody and a human immunoglobulin constant region. The term is also intended to include antibodies having a variable region derived from one human antibody grafted to an immunoglobulin constant region of a predetermined sequences or the constant region from another human for which there are allotypic differences residing in the constant regions of any naturally occurring antibody having the variable regions, e.g., CDRs 1, 2, and 3 of the light and heavy chain. Human heavy chain genes exhibit structural polymorphism (allotypes) that are inherited as a haplotype. The serologically defined allotypes differ within and between population groups. See Jefferis et al. mAb, 1 (2009), pp. 332-338.

In certain embodiments, the antibody, antigen binding fragment, the light chain, or the heavy chain comprises a non-naturally occurring chimeric amino acid sequence such that there is at least one mutation that is not present in naturally occurring antibodies comprising one or all of the six CDRs.

In certain embodiments, the antibody, antigen binding fragment, or heavy chain, comprises a human constant domain from an immunoglobulin constant region (Fc) having one, two, three, four, five, six, seven, eight, nine, ten, eleven, twelve, thirteen, fourteen, fifteen or more of the following mutations G236A, S239D, A330L, I332E, S267E, L328F, P238D, H268F, S324T, S228P, G236R, L328R, L234A, L235A, M252Y, S254T, T256E, M428L, N434S, P329G, D265A, N297A, N297G, N297Q, F243L, R292P, Y300L, V305I, P396L, S298A, E333A, K334A, L234Y, L235Q, G236W, S239M, H268D, D270E, K326D, A330M, K334E, K326W, E333S, E345R, E430G, S440Y, L235E, N325S. With regard to IgG Fc mutations reported herein, the sequences are in reference to following, amino acid sequence (SEQ ID NO: 137) starting at amino acid 119:

```
STKGPSVFP LAPSSKSTSG GTAALGCLVK DYFPEPVTVS WNSGALTSGV HTFPAVLQSS  178

GLYSLSSVVT VPSSSLGTQT YICNVNHKPS NTKVDKKVEP KSCDKTHTCP PCPAPELLGG  238

PSVFLFPPKP KDTLMISRTP EVTCVVVDVS HEDPEVKFNW YVDGVEVHNA KTKPREEQYN  298

STYRVVSVLT VLHQDWLNGK EYKCKVSNKA LPAPIEKTIS KAKGQPREPQ VYTLPPSRDE  358

LTKNQVSLTC LVKGFYPSDI AVEWESNGQP ENNYKTTPPV LDSDGSFFLY SKLTVDKSRW  418

QQGNVFSCSV MHEALHNHYT QKSLSLSPG.
```

It is noted that in reference to SEQ ID NO: 137, it is specifically for IgG1. IgG2, IgG3, and IgG4 will have some alternative amino acids as the same positions. For example, IgG2 contains a V at position 309 instead of L at position 309 for IgG1. IgG4 contains a F at position 234 instead of L at position 234 for IgG1.

In certain embodiments, this disclosure relates to antibodies reported wherein the constant region comprises a mutation that activates immune responses, enhance ADC by increasing FcγRIIIa binding or decreasing FcγRIIb binding, enhance ADCP by increasing FcγRIIa binding or increased FcγRIIIa binding, enhance CDC by increasing C1q binding or hexamerization, reduce effector functions by aglycosylation, reducing FcγR and C1q binding, increasing coengagement by increasing FcγRIIb binding, increasing FcγRIIa binding, or decreasing FcγRIIIa binding, and/or increases half-life.

In certain embodiments, this disclosure relates to antibodies reported wherein the constant region comprises a mutation in the Fc domain selected from L234A and L235A, or both.

In certain embodiments, this disclosure relates to antibodies reported wherein the constant region comprises a mutation in the Fc domain selected from L234A, L235A, and P329G, or all or combinations thereof.

In certain embodiments, this disclosure relates to antibodies reported wherein the constant region comprises a mutation in the Fc domain selected from D265A and N297A, or both.

In certain embodiments, this disclosure relates to antibodies reported wherein the constant region comprises a mutation in the Fc domain selected from D265A and N297G, or both.

In certain embodiments, this disclosure relates to antibodies reported wherein the constant region comprises a mutation in the Fc domain selected from D265A and N297Q, or both.

In certain embodiments, this disclosure relates to antibodies reported wherein the constant region comprises a mutation in the Fc domain selected from M252Y, S254T, T256E, or all or combinations thereof.

In certain embodiments, this disclosure relates to antibodies reported wherein the constant region comprises a mutation in the Fc domain selected from F243L, R292P, Y300L, V305I, P396L, or combinations thereof.

In certain embodiments, this disclosure relates to antibodies reported wherein the constant region comprises a mutation in the Fc domain selected from S239D, I332E or both.

In certain embodiments, this disclosure relates to antibodies reported wherein the constant region comprises a mutation in the Fc domain selected from S239D, I332E, A330L, or all or combinations thereof.

In certain embodiments, this disclosure relates to antibodies reported wherein the constant region comprises a mutation in the Fc domain selected from S239D, I332E, G236A, A330L, or all or combinations thereof.

In certain embodiments, this disclosure relates to antibodies reported wherein the constant region comprises a mutation in the Fc domain selected from S298A, E333A, K334A, or all or combinations thereof.

In certain embodiments, this disclosure relates to antibodies reported wherein the constant region comprises a mutation in the Fc domain selected from S298A, E333A, K334A, or all or combinations thereof.

In certain embodiments, this disclosure relates to antibodies reported wherein the constant region comprises a mutation in the Fc domain selected from L234Y, L235Q, G236W, S239M, H268D, D270E, S298A, or all or combinations thereof.

In certain embodiments, this disclosure relates to antibodies reported wherein the constant region comprises a mutation in the Fc domain selected from D270E, K326D, A330M, K334E, or all or combinations thereof.

In certain embodiments, this disclosure relates to antibodies reported wherein the constant region comprises a mutation in the Fc domain selected from G236A, S239D, I332E, or all or combinations thereof.

In certain embodiments, this disclosure relates to antibodies reported wherein the constant region comprises a mutation in the Fc domain selected from K326W, E333S or both.

In certain embodiments, this disclosure relates to antibodies reported wherein the constant region comprises a mutation in the Fc domain selected from E345R, E430G, S440Y, or all or combinations thereof.

In certain embodiments, this disclosure relates to antibodies reported wherein the constant region comprises a mutation in the Fc domain selected from E345R, E430G, S440Y, or all or combinations thereof.

In certain embodiments, this disclosure relates to antibodies reported wherein the constant region comprises a mutation in the Fc domain selected from F234A, L235A or both of IgG4.

In certain embodiments, this disclosure relates to antibodies reported wherein the constant region comprises a mutation in the Fc domain selected from H268Q, V309L, A330S, P331S or all or combinations thereof of IgG2.

In certain embodiments, this disclosure relates to antibodies reported wherein the constant region comprises a mutation in the Fc domain selected from V234A, G237A, P238S, H268A, V309L, A330S, P331S, or all or combinations thereof of IgG2.

FcgRIIb has immunosuppressive function. In certain embodiments, this disclosure relates to antibodies reported wherein the constant region comprises a mutation in the Fc domain selected from S267E, L328F or both.

In certain embodiments, this disclosure relates to antibodies reported wherein the constant region comprises a mutation in the Fc domain selected from S267E, L328F, P238D, or combinations thereof.

In certain embodiments, this disclosure relates to antibodies reported wherein the constant region comprises a mutation in the Fc domain selected from N325S and L328F or both.

Antibodies interact with the complement cascade through C1q binding enabling antibodies to activate complement-dependent cytotoxicity (CDC). In certain embodiments, this disclosure relates to antibodies reported wherein the constant region comprises a mutation that effectively active complement-dependent cytotoxicity such as those selected from S267E, H268F, S324T, or all or combinations thereof.

In certain embodiment interaction with the immune system through Fc receptors may be unnecessary or undesirable, i.e., immune-silent antibodies. In certain embodiments, this disclosure relates to antibodies reported wherein the constant region comprises a mutation that bind the antigen but do not bind to FcgRs such as those selected from S228P, G236R, L328R, L234A, L235A, or all or combinations thereof.

In certain embodiments, this disclosure relates to antibodies reported wherein the constant region comprises a mutation in the Fc domain selected from M428L, N434S or both.

In certain embodiments, is may be desirable to have antibodies wherein constant region of the Fc has been to increase or decrease antibody half-life. In certain embodiments, this disclosure relates to antibodies reported wherein the constant region comprises a mutation that increases or decreases the antibodies half-life such as those selected from M252Y, S254T, T256E, M428L, N434S or all or combinations thereof.

In certain embodiments, this disclosure contemplates that a heavy chain contains at least one mutation wherein both heavy chains are not identical. In certain embodiments, this disclosure contemplates that one heavy chain may have alternative mutations than the opposite heavy chain, i.e., one of the two heavy chains contain a mutation that the other sequence does not, or one of the two heavy chains contain one or more mutations and the other heavy chain contains different mutations.

In certain embodiments, this disclosure relates to antibodies reported wherein one constant region comprises a mutation in the Fc domain selected from L234Y, L235Q, G236W, S239M, H268D, D270E, S298A, or all or combinations thereof and the opposite constant region comprises a mutation in the Fc domain selected from D270E, K326D, A330M, K334E, or all or combinations thereof.

In certain embodiments, this disclosure relates to antibodies reported wherein one constant region is IgG2. In certain embodiments, this disclosure relates to antibodies reported wherein one constant region is IgG1 and the opposite constant region is IgG2. In certain embodiments, this disclosure relates to antibodies reported wherein one constant region is IgG1 and the opposite constant region is IgG3. In certain embodiments, this disclosure relates to antibodies reported wherein one constant region is IgG2 and the opposite constant region is IgG4.

In certain embodiments, this disclosure relates to antibodies reported wherein one constant region comprises a mutation in the IgG1 Fc domain selected from L234A, L235A, or both and the opposite constant region comprises a mutation in the IgG4 Fc domain selected from F234A, L235A, or both.

The disclosure particularly contemplates the production and use of "derivatives" of any of the above-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies, as well as variants having altered CH1, hinge, CH2, CH3 or CH4 regions, so as to form, for example antibodies, etc., having variant Fc regions that exhibit enhanced or impaired effector or binding characteristics.

The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification.

Carbohydrate modifications that lead to altered antibody mediated effector function are well known in the art (for example, see Shields, R. L. et al. (2002) "Lack of Fucose on Human IgG N-Linked Oligosaccharide Improves Binding to Human Fcγ RIII and Antibody-Dependent Cellular Toxicity," J. Biol. Chem. 277(30): 26733-26740; Davies J. et al. (2001) "Expression of GnTIII in a Recombinant Anti-CD20 CHO Production Cell Line: Expression of Antibodies with Altered Glycoforms Leads to an Increase In ADCC Through Higher Affinity For FC Gamma RIII," Biotechnology & Bioengineering 74(4): 288-294). Methods of altering carbohydrate contents are known to those skilled in the art, see, e.g., Wallick, S. C. et al. (1988) "Glycosylation of a VH Residue of a Monoclonal Antibody Against Alpha (1-6) Dextran Increases its Affinity for Antigen," J. Exp. Med. 168(3): 1099-1109; Tao, M. H. et al. (1989) "Studies of Aglycosylated Chimeric Mouse-Human IgG. Role of Carbohydrate in the Structure and Effector Functions Mediated by the Human IgG Constant Region," J. Immunol. 143(8): 2595-2601; Routledge, E. G. et al. (1995) "The Effect of Aglycosylation on the Immunogenicity of a Humanized Therapeutic CD3 Monoclonal Antibody," Transplantation 60(8):847-53; Elliott, S. et al. (2003) "Enhancement of Therapeutic Protein in Vivo Activities Through Glycoengineering," Nature Biotechnol. 21:414-21; Shields, R. L. et al. (2002) "Lack of Fucose on Human IgG N-Linked Oligosaccharide Improves Binding to Human Fcγ RIII and Antibody-Dependent Cellular Toxicity," J. Biol. Chem. 277(30): 26733-26740).

In some embodiments, a humanized antibody is a derivative. Such a humanized antibody comprises amino acid residue substitutions, deletions or additions in one or more CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present disclosure or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The VZV virus antibodies can be engineered to increase biological half-lives (see, e.g. U.S. Pat. No.

6,277,375). For example, VZV virus antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethylene glycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The term "recombinant" as used herein refers to an antibody produced by recombinant means, such as isolation of immunoglobulin sequences from human cells and their expression in transfected cells.

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, but would not bind to a totally unrelated antigen. Preferably, however, antibodies (and their antigen binding fragments) will not cross-react with other antigens. Antibodies may also bind to other molecules in a way that is not immune specific, such as to FcR receptors, by virtue of binding domains in other regions/domains of the molecule that do not involve the antigen recognition site, such as the Fc region.

The term "substantially," as used in the context of binding or exhibited effect, is intended to denote that the observed effect is physiologically or therapeutically relevant. Thus, for example, a molecule is able to substantially block an activity of an varicella-zoster virus if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete).

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize differentiated somatic cells transfected with a DNA expression vector that contains the template. The cells are cultured under conditions such that they translate the desired protein. Expressed proteins are extracted for subsequent purification. In vivo protein expression systems using prokaryotic and somatic eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive a subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

As used herein, the term "combination with" when used to describe administration with an additional treatment means that the agent may be administered prior to, together with, or after the additional treatment, or a combination thereof.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

Host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant varicella-zoster virus antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present disclosure include those disclosed in Brinkman, U. et al. (1995) "Phage Display Of Disulfide-Stabilized Fv Fragments," J. Immunol. Methods, 182:41-50, 1995; Ames, R. S. et al. (1995) "Conversion Of Murine Fabs Isolated From A Combinatorial Phage Display Library To Full Length Immunoglobulins," J. Immunol. Methods, 184:177-186; Kettleborough, C. A. et al. (1994) "Isolation Of Tumor Cell-Specific Single-Chain Fv From Immunized Mice Using Phage-Antibody Libraries And The Re-Construction Of Whole Antibodies From These Antibody Fragments," Eur. J. Immunol., 24:952-958, 1994; Persic, L. et al. (1997) "An Integrated Vector System For The Eukaryotic Expression Of Antibodies Or Their Fragments After Selection From Phage Display Libraries," Gene, 187:9-18; Burton, D. R. et al. (1994) "Human Antibodies From Combinatorial Libraries," Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art (such as those disclosed in PCT Publication WO 92/22324; Mullinax, R. L. et al. (1992) "Expression Of A Heterodimeric Fab Antibody Protein In One Cloning Step," BioTechniques, 12(6):864-869; and Sawai et al. (1995) "Direct Production Of The Fab Fragment Derived From The Sperm Immobilizing Antibody Using Polymerase Chain Reaction And cDNA Expression Vectors," Am. J. Reprod. Immunol. 34:26-34; and Better, M. et al. (1988) "*Escherichia coli* Secretion of an Active Chimeric Antibody Fragment," Science 240:1041-1043). Examples of techniques which can be used to produce single-chain Fvs and antibodies include those described in U.S. Pat. Nos. 4,946,778 and 5,258,498; Huston, J. S. et al. (1991) "Protein Engineering of Single-Chain Fv Analogs and Fusion Proteins," Methods in Enzymology 203:46-88; Shu, L. et al., "Secretion of a Single-Gene-Encoded Immunoglobulin from Myeloma Cells," Proc. Natl. Acad. Sci. (USA) 90:7995-7999; and Skerra. A. et al. (1988) "Assembly of a Functional Immunoglobulin Fv Fragment in Escherichia coli," Science 240:1038-1040.

Antibodies interact with the complement cascade through C1q binding enabling antibodies to activate complement-dependent cytotoxicity (CDC). In certain embodiments, this disclosure relates to antibodies that exhibit an improved ability neutralize varicella-zoster virus infectivity and prevent cell-to-cell spread when complement is present.

The molecules of the present disclosure may be attached to solid supports, which are particularly useful for immunoassays or purification of the target antigen or of other molecules that are capable of binding to target antigen that has been immobilized to the support via binding to an antibody or antigen-binding fragment of the present disclosure. Such solid supports include, but are not limited to, glass, cellulose, polyacrylamide, nylon, polystyrene, polyvinyl chloride or polypropylene.

The present disclosure additionally includes nucleic acid molecules (DNA or RNA) that encode any such antibodies, fusion proteins or fragments, as well as vector molecules (such as plasmids) that are capable of transmitting or of replication such nucleic acid molecules and expressing such antibodies, fusion proteins or fragments in a cell line. The nucleic acids can be single-stranded, double-stranded, may contain both single-stranded and double-stranded portions.

Varicella-Zoster Virus and ZOSTAVAX® Vaccination in Humans

Varicella-zoster virus is a human herpesvirus that causes chickenpox upon primary infection, a disease characterized by rash, itching, and blisters. Once this acute infection is controlled, the virus remains dormant in nerve ganglia for the duration of the infected individual's life. When the latently infected individual becomes immunocompromised, the virus can emerge from latency and begin replicating. This reactivated infection causes the disease shingles, which is characterized by a painful rash.

Varicella-zoster virus particles are composed of genomic DNA, a lipid envelope, and multiple glycoproteins that mediate viral entry and pathogenesis. The majority of the immune response to varicella-zoster virus targets these glycoproteins, specifically glycoprotein E.

Immunization with varicella vaccine (Varivax®) can prevent primary infection and chicken pox from occurring in young children, and immunization with zoster vaccine (Zostavax®) can reduce the likelihood of developing shingles in individuals that have already had chickenpox. Treatment of active infection, however, is currently limited to the use of antiviral drugs such as acyclovir, valaciclovir, and famaciclovir with limited efficacy.

Described herein are recombinant (human monoclonal) antibodies that bind specifically to glycoproteins of varicella-zoster virus. These antibodies were derived from plasmablasts of individuals vaccinated with a live attenuated varicella-zoster vaccine. While glycoprotein E is the most abundant glycoprotein on the surface of varicella-zoster virus and the predominant target of the antibody response following vaccination, antibodies to glycoprotein H have more potent neutralization activity and can inhibit viral spread between cells. In certain embodiments, this disclosure relates to recombinant chimeric antibodies, wherein the antibody comprises a heavy chain having a variable and constant region and a light chain having a variable and constant region, and wherein the antibody specifically binds glycoproteins of varicella-zoster virus Molecular techniques were used to examine the functionality of the VZV-specific response after ZOSTAVAX® vaccination in humans. Whether VZV-specific antibodies play a role in in vitro protection was evaluated. The humoral response induced by ZOSTAVAX® is predominately a memory B cell recall response: it is composed of IgG and IgA ASCs, with no detectible IgM ASCs, and shows levels of somatic hypermutation similar to what is seen after seasonal influenza vaccination. The majority of antibodies were specific to VZV gE (60%), indicating that gE is the predominant antibody target after vaccination. Specific gI monoclonal antibodies were detected (20%). These MAbs recognized gI, as determined by SDS-PAGE and Western blotting, but some appeared to coprecipitate gE. Three gB-specific antibodies (12%) and two gH antibodies (8%) (1 from RM and 1 from ZV303) were detected. Functional analyses of these antibodies demonstrated that the gH-specific MAbs were the most potent neutralizers (with or without complement) and could also inhibit cell-to-cell spread of VZV in vitro.

Neutralization $IC_{50}$ for the gH antibodies generated in this study were 0.03 to 0.23 µg/ml (0.2 to 1.5 nM). One gB antibody (303-1C2) could also neutralize VZV in vitro with or without complement. However, 303-1C2 was much less potent than the gH MAbs (without complement, 16.6 times less potent; with complement, 73 times less potent). VZV gE-specific MAbs could neutralize in vitro only in the presence of complement but could not inhibit cell spread.

VZV-specific monoclonal antibodies may be generated by (i) hybridoma generation after immunization of mice with VZV, (ii) fusion of Ig V genes from mouse hybridomas to human Ig constant regions, (iii) in vitro immunization of human lymphocytes with VZV antigens, followed by fusion of the lymphocytes to myeloma cells, or (iv) phage display panning of a library of human Ig genes derived from human splenocytes obtained from subjects with idiotypic thrombocytopenic purpura.

Antibodies can act through a variety of mechanisms to prevent virus entry, including blocking receptor engagement, preventing post-binding/prefusion events at the cell surface or inside endosomes, inhibiting release of progeny virus, opsonization, antibody-dependent cell-mediated cytotoxicity (ADCC), and activation of the complement cascade. As gH/gL and gB are important for virion fusion, antibodies directed against these glycoproteins are likely to prevent viral attachment and thus interfere with cell-to-cell spread. VZV-specific gE antibodies neutralize in a complement-dependent manner but do not inhibit cell-to-cell spread. One possible mechanism for this is that binding of gE-specific antibodies to VZV particles leads to the activation of the complement cascade and inactivation of the virus, while infected cells are protected from complement-mediated lysis due to the presence of complement regulatory proteins on the cell surface and/or low cell surface expression of gE.

The antibodies that were detected after ZOSTAVAX® vaccination had a high degree of somatic hypermutations (median, 20; range, 7 to 34). It is unclear whether these mutations were a result of primary infection, exogenous exposure to varicella, or subclinical reactivation over time. These data suggest that subclinical reactivation and subsequent boosting of the immune response may occur as people age. Since there are similar degrees of somatic hypermutation observed after vaccination with ZOSTAVAX® and with seasonal influenza vaccine, endogenous/exogenous boosting of the VZV-specific memory B cell compartment could result in increased affinity maturation over time.

Treatment of immunocompromised children and pregnant women with high-titer VZV polyclonal sera is reported to prevent severe varicella. There are limited data evaluating whether VZV-specific neutralizing antibody titers or gH-specific antibody titers decrease with age. If the neutralizing antibody titers do not decrease with age, this would be further evidence that antibodies probably do not play a protective role against the development of shingles. It could be envisaged that antibodies may play a protective role in preventing disseminated VZV during primary infection when the virus titer in the blood is high.

Evidence in this report demonstrates that gE antibodies can neutralize in the presence of complement in vitro but cannot inhibit cell-to-cell spread. The FDA-approved VZV vaccine Shingrix is a subunit vaccine containing VZV gE adjuvanted with ASO1B. Experiments indicate that gE-specific antibodies are not the most functionally potent VZV-specific antibodies (compared to gH-specific antibodies) in terms of neutralization and cell-to-cell spread. Thus, unless the ASO1B adjuvant induces a gE antibody qualitatively different from what natural infection/ZOSTAVAX® vaccination induces (i.e., can inhibit cell-to-cell spread) or acts differently in vivo where there is complement present, the most likely mechanism of protection for Shingrix could be attributed to T cells.

Human VZV-specific antibodies were identified via an unbiased approach from 5 separate subjects 7 days after receiving ZOSTAVAX®. Donors tested had gE-specific MAbs, and they were either the only antibody isolated (301 and 304) or the predominant antibody (RM, 302, and 303). Although the majority of antibodies were VZV gE specific, the most potent antibodies in vitro were directed against gH. If antibodies do play a protective role in vivo during chickenpox or shingles, then inclusion of gH (gH/gL) protein would be beneficial. Additionally, gH-specific monoclonal antibody therapy is alternative to VariZIG in VZV-negative immunocompromised patients or pregnant women.

Therapeutic Methods and Compositions

In certain embodiments, the disclosure relates to methods of preventing or treating a varicella-zoster virus infection comprising administering an effective amount of a pharmaceutical composition disclosed herein to a subject in need thereof. In certain embodiments, the subject is at risk of, exhibiting symptoms of, or diagnosed with a varicella-zoster virus infection.

In certain embodiments, this disclosure relates to methods of treating or preventing a varicella-zoster infection comprising administering an effective amount of a recombinant chimeric antibody disclosed herein to a subject in need thereof. In certain embodiments, the antibodies are non-naturally occurring chimeric antibodies. In certain embodiments the subject is at high risk, immunocompromised, newborn of mother with varicella shortly before or after delivery, premature infant, infant less than one year of age, pregnant, or a subject without evidence of immunity.

In certain embodiments, this disclosure relates to methods of treating or preventing a varicella-zoster infection comprising administering an effective amount of a recombinant chimeric antibody disclosed herein to a subject in need thereof. In certain embodiments, the antibodies are non-naturally occurring chimeric antibodies. In certain embodiments the subject is at high risk, immunocompromised, newborn of mother with varicella shortly before or after delivery, premature infant, infant less than one year of age, pregnant, or a subject without evidence of immunity.

In certain embodiments, the subject is diagnosed with or without a previous varicella-zoster virus infection. In certain embodiments, the subject the subject has a compromised immune system or is diagnosed with agammaglobulinemia. In certain embodiments, the subject has cancer and is being administered a chemotherapy agent. In certain embodiments, the subject is pregnant without a previous varicella-zoster virus infection. In certain embodiments, the subject was born more than two or weeks before the estimated due date. In certain embodiments, the subject was born before the start of the 37th week of pregnancy. In certain embodiments, the subject is less than two-week, one month, six months, 1 year, 2 years 3 years, 4 years, or 5 years old. In certain embodiments, the subject is an organ transplant recipient. In certain embodiments, the subject is more than 55, 60, 65, or 70 years old.

In certain embodiments, the disclosure relates to methods of preventing or treating a varicella-zoster virus infection comprising administering an effective amount of a pharmaceutical composition comprising an antibody or antigen binding fragment disclosed herein to a subject in need thereof. Treatment of a subject with a therapeutically or prophylactically effective amount of antibody or antibody binding fragment can include a single treatment or, preferably, can include a series of treatments. In certain embodiments, the subject is at risk of, exhibiting symptoms of, or diagnosed with a varicella-zoster virus infection.

In certain embodiments, the antibody or antigen binding fragment is administered in combination with another therapeutic agent or antiviral agent. In certain embodiments, the antiviral agent(s) is abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, dolutegravir, edoxudine, efavirenz, emtricitabine, enfuvirtide, entecavir, famciclovir, fomivirsen, fosamprenavir, foscarnet, fosfonet, ganciclovir, ibacitabine, inosine acedoben dimepranol, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, saquinavir, stavudine, tenofovir, tenofovir disoproxil, tenofovir alafenamide fumarate, tipranavir, trifluridine, trizivir, tromantadine, valaciclovir, valganciclovir, vicriviroc, vidarabine, viramidine, zalcitabine, zanamivir, or zidovudine, and combinations thereof.

The dosages and frequencies of administration provided herein are encompassed by the terms therapeutically effective and prophylactically effective. The dosage and frequency further will typically vary according to factors specific for each patient depending on the specific therapeutic or prophylactic agents administered, the severity, the route of administration, as well as age, body weight, response, and the past medical history of the patient. Suitable regimens can be selected by one skilled in the art by considering such factors and by following, for example, dosages reported in the literature and recommended in the Physician's Desk Reference (56th Ed., 2002).

Various delivery systems are known and can be used to administer the therapeutic or prophylactic compositions, e.g., encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

Methods of administering antibodies and antigen binding fragments include, but are not limited to, parenteral administration (e.g., intradermal, intramuscular, intraperitoneal, intravenous and subcutaneous), epidural, and mucosal (e.g., intranasal and oral routes). In a specific embodiment, the antibodies or fusion proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as silastic membranes, or fibers.

In some embodiments, the antibodies or antigen binding fragments are formulated in liposomes for targeted delivery of the antibodies or fusion proteins. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the disclosure, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

Methods of preparing liposomes with a prolonged serum half-life, i.e., enhanced circulation time, such as those disclosed in U.S. Pat. No. 5,013,556 can be used to make liposomes-antibody compositions. Preferred liposomes are not rapidly cleared from circulation, i.e., are not taken up into the mononuclear phagocyte system (MPS). The disclosure encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces opsonization with serum components and reduces recognition by MPS. Sterically stabilized liposomes are preferably prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309. The disclosure also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the disclosed compositions and methods can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody, e.g., F(ab'), may be conjugated to the liposomes using previously described methods, see, e.g., Martin et al., 1982, J. Biol. Chem. 257: 286-288.

The antibodies, or antigen binding fragments may also be formulated as immunoliposomes. Immunoliposomes refer to a liposomal composition, wherein an antibody or a fragment thereof is linked, covalently or non-covalently to the liposomal surface. The chemistry of linking an antibody to the liposomal surface is known in the art and encompassed within the disclosure, see, e.g., U.S. Pat. No. 6,787,153; Allen et al., 1995, Stealth Liposomes, Boca Rotan: CRC Press, 233-44; Hansen et al., 1995, Biochim. Biophys. Acta, 1239: 133-144. In most preferred embodiments, immunoliposomes for use in the disclosed methods and compositions are further sterically stabilized. Preferably, the antibodies or antigen binding fragments are linked covalently or non-covalently to a hydrophobic anchor, which is stably rooted in the lipid bilayer of the liposome. Examples of hydrophobic anchors include, but are not limited to, phospholipids, e.g., phosphatidylethanolamine (PE), phosphatidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionyl-phosphatidylethanolamine. See, e.g., Dietrich et al., 1996, Biochemistry, 35: 1100-1105; Loughrey et al., 1987, Biochim. Biophys. Acta, 901: 157-160; Martin et al., 1982, J. Biol. Chem. 257: 286-288; Martin et al., 1981, Biochemistry, 20: 4429-38. Although not intending to be bound by a particular mechanism of action, immunoliposomal formulations including an antibody or fusion protein are particularly effective as therapeutic agents, since they deliver the antibody or fusion protein to the cytoplasm of the target cell, i.e., the cell comprising the receptor to which the antibody or fusion protein binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions include one or more vesicle forming lipids, an antibody or a fragment or derivative thereof or a fusion protein, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides.

Additional lipids useful in the formulations are known to one skilled in the art and encompassed within the disclosure. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the disclosure. For a review of immunoliposomes and methods of preparing them, see, e.g., U.S. Patent Application Publication No. 2003/0044407; PCT International Publication No. WO 97/38731, Vingerhoeads et al., 1994, Immunomethods, 4: 259-72; Maruyama, 2000, Biol. Pharm. Bull. 23(7): 791-799; Abra et al., 2002, Journal of Liposome Research, 12(1&2): 1-3; Park, 2002, Bioscience Reports, 22(2): 267-281; Bendas et al., 2001 BioDrugs, 14(4): 215-224, J. Thomas August, ed., 1997, Gene Therapy: Advances in Pharmacology, Volume 40, Academic Press, San Diego, Calif., p. 399-435.

The antibodies and antigen binding fragments can be packaged in a hermetically sealed container, such as an ampoule or sachet, indicating the quantity of antibody. In one embodiment, the antibodies are supplied as a dry sterilized lyophilized powder or water free concentrate in a hermetically sealed container and can be reconstituted, e.g., with water or saline to the appropriate concentration for administration to a subject. Preferably, the antibodies or fusion proteins are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies or antigen binding fragments should be stored at between 2 and 8° C. in their original container and the antibodies should be administered within 12 hours, preferably within 6 hours, within 5 hours, within 3 hours, or within 1 hour after being reconstituted. In an alternative embodiment, antibodies or fusion proteins are supplied in liquid form in a hermetically sealed container indicating the quantity and concentration of the antibody, fusion protein, or conjugated molecule. Preferably, the liquid form of the antibodies or fusion proteins are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies of fusion proteins.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies or fragments thereof, or fusion proteins may be reduced by enhancing uptake and tissue penetration of the antibodies or fusion proteins by modifications such as, for example, lipidation.

In certain embodiments, the therapeutic or prophylactic composition is a nucleic acid encoding a varicella-zoster antibody or an antigen-binding fragment thereof. The nucleic acid can be administered in vivo to promote expression of its encoded antibody or fragment, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, the disclosed compositions include a prophylactically or therapeutically effective amount of antibody or fusion protein and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with antibody or antigen binding fragment. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

The present disclosure provides kits that can be used in the above methods. In one embodiment, a kit comprises one or more antibodies or antigen binding fragments. In another embodiment, a kit further comprises one or more other prophylactic or therapeutic agents useful for the treatment of varicella-zoster infection, in one or more containers.

Examples

Described herein are recombinant (human monoclonal) antibodies that bind specifically to glycoproteins of varicella-zoster virus. These antibodies were derived from plasmablasts of individuals vaccinated with a live attenuated varicella-zoster vaccine. While glycoprotein E is the most abundant glycoprotein on the surface of varicella-zoster virus and the predominant target of the antibody response following vaccination, antibodies to glycoprotein H have more potent neutralization activity and can inhibit viral spread between cells.

Disclosed herein are monoclonal antibodies specific to glycoprotein H of varicella-zoster virus that can be used as a neutralizing antibody, prophylactic treatment of patients at risk of developing shingles, or therapeutic treatment of patients experiencing symptoms of shingles. To develop these antibodies, circulating B cells were isolated from the blood patients enrolled in a clinical trial testing the varicella-zoster vaccine (ZOSTAVAX®). Plasmablasts were sorted individually so that sequences encoding the heavy chain and light chain of virus-specific antibodies could be amplified by PCR, then cloned into expression vectors. Antibodies were produced by cells transfected with these expression vectors, then functional analysis was conducted to evaluate the ability of these antibodies to neutralize varicella-zoster virus in vitro. This functional analysis revealed two antibodies that target glycoprotein H of varicella-zoster virus, in contrast to glycoprotein E, which is targeted by the majority of the antibody response to this virus. These glycoprotein H-specific antibodies were able to neutralize varicella-zoster virus infectivity in vitro, as well as prevent cell-to-cell spread.

TABLE 1

Data for certain antibodies.

| Antibody Name | Specificity | Immunoprecipitation Product | In vitro neutralization $IC_{50}$ (with complement) | In vitro neutralization $IC_{50}$ (without complement) |
| --- | --- | --- | --- | --- |
| RM-2D6 | Glycoprotein H | Glycoprotein H | 0.03 µg/mL | 0.23 µg/mL |
| 302-1G9 | Glycoprotein H | Glycoprotein H/L | 0.06 µg/mL | 0.09 µg/mL |

Neutralizing Antibodies and their Properties

Antibody RM-2D6 neutralizes varicella-zoster virus infection of cells at $IC_{50}$ 0.03 µg/mL with complement and 0.23 µg/mL in the presence of complement. Immunoprecipitation using this antibody recovers only glycoprotein H. In vitro neutralization is a test of an antibody's capacity to prevent virus from infecting cells in a tissue culture system. Number represents the concentration of antibody necessary to prevent infection in 50% of cells when a mixture of antibody/varicella-zoster virus was used to inoculate cells.

Antibody 302-1G9 neutralizes varicella-zoster virus infection of cells at $IC_{50}$ 0.06 µg/mL with complement and 0.09 µg/mL in the presence of complement. Immunoprecipitation using this antibody recovers glycoprotein H/L complex.

Both antibodies block 100% of cell-to-cell spread in vitro at 10 µg/mL, with $IC_{50}$ values µ1.4-6.2 µg/mL.

Methods for Production of the Antibodies

Wrammert et al. (Nature, 2008, 453:667-671) report using immunoglobulin variable regions isolated from sorted single ASCs to produce human monoclonal antibodies (mAbs) that bound with high affinity. Smith et al. (Nat Protoc, 2009, 4:372-384) report a protocol for the production of antigen-specific human monoclonal antibodies (hmAbs) wherein antibody-secreting cells (ASCs) are isolated from whole blood collected after vaccination and sorted by flow cytometry into single cell plates. The antibody genes of the ASCs are then amplified by RT-PCR and nested PCR, cloned into expression vectors and transfected into a human cell line.

Antibody Secreting Cell (ASC) Sorting

Freshly isolated PBMC from ~40 mL of blood was stained with anti-human CD19 FITC (BD 555412), anti-human CD38 PE (BD 555460), anti-human CD3 PECY7 (BD 557851), anti-human CD20 PE-Cy7 (BD 335793) and anti-human CD27 APC (ebio 17-0279) for 30 minutes on ice. Cells were washed and resuspended in PBS+2% FBS. Using a BD FACS Aria II, antibody secreting cells (CD19+ CD38+CD27+) were either single cell sorted into a 96 well PCR plate containing 10 mM Tris-HCL with 40 U/ul of RNAse inhibitor (Promega) and frozen at −80° C. or bulk sorted into complete media.

Generation of Monoclonal Antibodies

The generation of monoclonal antibodies from single-cell sorted ASCs was performed. IgG and IgA heavy, kappa and lambda variable regions were amplified by reverse transcription and PCR. cDNA was synthesized from random hexamers and used for a 1st round IgGH, IgAH/IgMH, Igx and Igλ, PCR. The 1st round PCR cocktail of primers covered all families of variable (V) and joining (J) genes, followed by a nested PCR to identify the sequences of the V and J genes of the IgGH, IgAH/IgMH, Igx and Igλ, regions. Once the IgGH, IgAH/IgMH, Igx and Igλ, gene families were known, highly specific primers were used to amplify these regions and put restriction enzyme sites for cloning into IgG1H, Igx and Igλ, backbones for antibody expression. These antibodies were expressed in HEK293 (RM) or Expi293 (donors 301, 302, 303, 304) cells. The antibodies were affinity purified using protein A agarose beads.

VZV Lysate and gE-Specific ELISAs

Binding specificity of isolated monoclonal antibodies was determined by ELISA. An initial VZV infected cell lysate ELISA was performed. If VZV lysate+, a VZV total glycoprotein ELISA was used to identify VZV gP-specific mAbs. A follow-up VZV gE ELISA was utilized for those mAbs showing specificity for VZV glycoproteins.

For the VZV infected cell lysate and gP ELISA, Nunc C96 Maxisorp™ Immunoplates (Thermo Scientific) were coated overnight at 4° C. with either VZV infected cell lysate (Meridian Life Sciences 7740) or lectin purified VZV glycoproteins (Virusys or in-house reagent) diluted in PBS at a concentration of 1 µg/mL. For the VZV gE ELISA, Pierce nickel-coated plates (Thermo Scientific) were coated overnight at 4° C. with His-tagged recombinant VZV gE protein (Oka strain, in-house reagent) diluted in PBS at a concentration of 1 µg/mL. The remainder of the protocol was identical for the VZV lysate, VZV total glycoprotein and VZV gE ELISAs. Protein coated plates were washed six times with PBS/0.05% Tween 20 and blocked with blocking buffer (PBS/0.05% Tween 20 with 3% non-fat dry milk) for 1 hour at room temperature on a plate rocker. Either supernatant from transiently transfected Expi293 cells diluted 1:2 in blocking buffer (VZV lysate ELISA) or VZV-specific monoclonal antibodies were 5-fold serially diluted in blocking buffer, starting at a concentration of 3 µg/mL, for a total of 4-6 dilutions. Blocking buffer was removed from the coated plates and diluted antibodies were bound to the plate for 1.5 hours at room temperature on a plate rocker. Antibody-bound plates were washed six times with PBS/0.05% Tween 20. Goat anti-human IgG-HRP (Southern Biotech) was diluted 1:2,000 in blocking buffer and added to the washed plates for 1 hour at room temperature on a plate rocker. Plates were washed six times with PBS/0.05% Tween 20 and developed for 5 minutes with SuperBlu-Turbo® TMB solution (Virolabs) followed by ELISA Stop Solution for TMB (Virolabs). Absorbance was read at OD450 nm on a VICTOR Multilabel Counter (Wallac/Perkin Elmer) and antibody binding curves were visualized using non-linear fit four parameter variable slope analysis in GraphPad Prism 7™ software.

Methods for Measuring Capacity of Antibodies to Neutralize Varicella-Zoster Virus Infectivity or Inhibit Cell-to-Cell Spread In Vitro.

GFP-VZV (pOKA ORF11-GFP) was kindly provided by Drs Marvin Sommer and Ann Arvin, Stanford University. GFP-tagged VZV Oka strain stocks were grown in MRC-5 cells. MRC-5 cells were cultured 35° C., 5% $CO_2$ in 2% complete EMEM; Eagle minimum essential medium (EMEM, Corning) supplemented with 2% heat-inactivated fetal bovine serum (Hyclone), 1% L-glutamine (Gibco), and 0.5% neomycin (Sigma). Cell-associated virus was harvested into PGS buffer (in-house buffer) at 40 hours post infection, sonicated to disassociate virus from cells, and centrifuged at 1,500 rpm for 10 minutes to remove cell debris. Cell-free virus was flash frozen in liquid nitrogen and stored at −70° C.

In Vitro Neutralization Assay

Purified VZV-specific monoclonal antibodies were 3-fold serially diluted, starting at a concentration of 25 µg/mL, for a total of 10 dilutions. Antibodies were diluted into 2% complete DMEM/F-12; Dulbecco's modification of Eagle's medium/Ham's F-12 50/50 mix (DMEM/F-12, Corning) supplemented with 2% heat-inactivated fetal bovine serum (Hyclone) and 1% penicillin-streptomycin (Corning). GFP-tagged VZV Oka strain stocks were quick-thawed in a water bath, diluted to a concentration of 300 pfu/25 µL in PGS buffer, and kept on wet ice. 25 µL of diluted antibody was thoroughly mixed with 25 µL of diluted VZV-GFP (giving a final starting antibody concentration of 12.5 µg/mL) in a flat-bottom, clear-walled 96-well plate (Costar 3598) and incubated at 35° C., 5% $CO_2$ for 1 hour. Controls included VZV-GFP alone (no antibody) and blank wells (no antibody and no VZV-GFP). After 1 hour of incubation, 10 units/well of reconstituted guinea pig complement (Sigma) was added to half of the virus/antibody wells (totaling 4 replicates per condition) and incubated at 35° C., 5% $CO_2$ for an additional 30 minutes. ARPE-19 target cells were diluted in 2% complete DMEM/F-12 and 20,000 cells, in 50 µl, were added to each well, mixed thoroughly, and incubated at 35° C., 5% $CO_2$ for 1 hour with shaking every 15 minutes. 100 µl of 2% complete DMEM/F-12 was then added to each well and the plate was centrifuged at 1,200 rpm for 10 minutes to encourage virus-cell interaction and cell settling. The plate was incubated at 35° C., 5% $CO_2$ for 5-7 day and the total number of cells expressing GFP per well was quantified using an Acumen® CELLISTA (TTP LabTech). The percent of viral neutralization for each well was defined as ((average of 4 replicates of VZV-GFP only control−condition of interest)/average of 4 replicates of VZV-GFP only control)× 100. $IC_{50}$ values were calculated from dilution curves using GraphPad Prism 7 software.

In Vitro Cell-to-Cell Spread Inhibition Assay

MRC-5 cells (100,000) (ATCC) per well were plated in a 12-well plates (Corning 3513) in 2 ml of complete Eagle's minimal essential medium (EMEM Sigma) with 10% fetal bovine serum, 1% of L-glutamine and 0.5% neomycin for 2-3 days at 37° C., 5% $CO_2$ until >90% confluency was reached. GFP-labeled cell free VZV was generated as discussed above (at $7.03 \times 10^4$ PFU/ml). MRC-5 confluent wells were washed 1× with warm complete EMEM+10% FBS media and 100 ul of 1:125 diluted VZV in PGS buffer (Merck in house) was added per well (~55 PFU/well). PGS buffer alone was added as a mock control. Plates were rocked back and forth 8× and incubated for 15 min at 35° C., 5% $CO_2$. This was repeated 3× for a total infection time of 1 hr. After 1 hr, 2 ml of EMEM+2% FBS+1% L-glutamine+ 0.5% neomycin was added and plates placed back at 35° C., 5% $CO_2$ for 16-18 hours. The next day, wells were washed 1× with warm 2 ml of EMEM+2% FBS+1% L-glutamine+ 0.5% neomycin and antibodies were diluted in EMEM+2% FBS+1% L-glutamine+0.5% neomycin starting at 30 ug/ml. 0.5 ml of diluted antibodies were added per well for 60 min at 35° C., 5% $CO_2$. For the complement treated wells, 65 ul of guinea pig complement (Sigma 51639) was added and incubated for 30 minutes at 35° C., 5% $CO_2$. 1.5 ml of EMEM+2% FBS+1% L-glutamine+0.5% neomycin was added and plates were placed back at 35° C., 5% $CO_2$ for 4 more days.

To fix and immunostain the cells, wells were washed with PBS and 2 ml of 90% acetone (Sigma 534064) diluted in distilled water was added for 10 min at room temperature. Wells were washed 1× with PBS and 0.5 ml of 1:2000 diluted VZV glycoprotein E antibody (Abcam Ab52549) in PBS+0.05% Tween 20 added for 30 min at 37° C. Wells were gently washed 2× with PBS and rabbit anti-mouse IgG peroxidase secondary antibody (Sigma A9044) diluted 1:1000 in PBS+0.05% Tween20 was added at 0.5 ml per well for 30 min at 37° C. Wells were washed 2× with PBS and 150 ul of 1×DAB/Metal in peroxide buffer (Thermo Scientific 1856090) was added, rocked back and forth 8× and incubated at room temperature for 15 min. Plates were then flipped over onto paper towels and dried overnight at room temperature. The plates were scanned on a CTL Immunospot™ S6 reader (Shaker Heights, Ohio). The percent of cell-to-cell spread inhibition for each condition was defined as ((average of 3 replicates of VZV-GFP only control−condition of interest)/average of 3 replicates of VZV-GFP only control)×100. $IC_{50}$ values were calculated from dilution curves using GraphPad Prism™ 7 software.

Antibody Sequences

Nucleic acid and amino acid sequences for antibodies disclosed herein are reported in GenBank under the following accession numbers (heavy/light chains):

RM-2D6, MH259730/MH259755 (respective CDRs 1-3):
(SEQ ID NO: 3)
GFMFSSYG, (SEQ ID NO: 4)
VSHDGTND, (SEQ ID NO: 1)
AKTSWARFLEWTFDY/

(SEQ ID NO: 5)
QSINRY, (SEQ ID NO: 6)
GASS, (SEQ ID NO: 2)
QQSHSTPT.

302-1G9, MH259712/MH259737 (respective CDRs 1-3):
(SEQ ID NO: 11)
GYTFSNYG, (SEQ ID NO: 12)
ISASNANT, (SEQ ID NO: 9)
ARDRGGSLAMVVGLDH/

(SEQ ID NO: 13)
QSIGGY, (SEQ ID NO: 14)
AAST,
and (SEQ ID NO: 10)
QQCYSAELT.

301-1G5, MH259708/MH259733 (respective CDRs 1-3):
(SEQ ID NO: 17)
GYRFTGYY, (SEQ ID NO: 18)
VNPQSGGT, (SEQ ID NO: 19)
ATLTRETGAPSTFDY/

(SEQ ID NO: 20)
HSVLNSANNKNY, (SEQ ID NO: 21)
WAST, (SEQ ID NO: 22)
QHYYNTPLT.

302-1B12, MH259709/MH259734 (respective CDRs 1-3):
(SEQ ID NO: 23)
GGTFGSHA, (SEQ ID NO: 24)
IIPILALV, (SEQ ID NO: 25)
ARGGSFSLGANGLDV/, (SEQ ID NO: 26)
QSVSSTY, (SEQ ID NO: 27)
GASR, (SEQ ID NO: 28)
QQHGSLPWT.

302-1C12, MH259710/MH259735 (respective CDRs 1-3):
(SEQ ID NO: 29)
GGTFSSYV, (SEQ ID NO: 30)
IIPMLGVS, (SEQ ID NO: 31)
AIRGGMTTLTPEDLDV/

(SEQ ID NO: 32)
QSLLHSDGKTY, (SEQ ID NO: 33)
QVSK, (SEQ ID NO: 34)
MQSIHLPLT.

302-1D11, MH259711/MH259736 (respective CDRS 1-3):
(SEQ ID NO: 35)
GFNFHEYG, (SEQ ID NO: 36)
INWNSGTI, (SEQ ID NO: 37)
AKDQYCGGDCHSKSYYYYGMDV/

(SEQ ID NO: 38)
SGSIASNY, (SEQ ID NO: 39)
EDNQ, (SEQ ID NO: 40)
QSYDSQTAVI.

303-1A8, MH259713/MH259738 (respective CDRs 1-3):
(SEQ ID NO: 41)
GFTFRTVA, (SEQ ID NO: 42)
ISHAGTSK, (SEQ ID NO: 43)
ARDGSFGLDY/

QGIRSD, (SEQ ID NO: 44)

GAST, (SEQ ID NO: 45)

LQDYNDPYT. (SEQ ID NO: 46)

303-1A12, MH259714/MH259739 (respective CDRs 1-3):

GFLFYSYG, (SEQ ID NO: 47)

ISGNGENT, (SEQ ID NO: 48)

ARDRDWNYFDK/ (SEQ ID NO: 49)

SSNIGSNA, (SEQ ID NO: 50)

VNHQ, (SEQ ID NO: 51)

AAWDDRLNGYV. (SEQ ID NO: 52)

303-1B2, MH259715/MH259740 (respective CDRs 1-3):

GGSINSGDFY, (SEQ ID NO: 53)

IYHGGGT, (SEQ ID NO: 54)

ARESIGDDFWSGLGP/ (SEQ ID NO: 55)

QSLLHSNGHNF, (SEQ ID NO: 56)

LGSN, (SEQ ID NO: 57)

MQALQTPYT. (SEQ ID NO: 58)

303-1C1, MH259716/MH259741 (respective CDRs 1-3):

GISVSSNY, (SEQ ID NO: 59)

TYSGGST, (SEQ ID NO: 60)

AREAYNSGTYYFDY/, (SEQ ID NO: 61)

QSISKS, (SEQ ID NO: 62)

AASS, (SEQ ID NO: 63)

QQSHTIPYT. (SEQ ID NO: 64)

303-1C2, MH259717/MH259742 (respective CDRs 1-3):

GFTLSSHD, (SEQ ID NO: 65)

ISYDGSNK, (SEQ ID NO: 66)

ARDFSGVTTISLDS/ (SEQ ID NO: 67)

SSNIGNNA, (SEQ ID NO: 68)

YDDK, (SEQ ID NO: 69)

AAWDDSLNRGV. (SEQ ID NO: 70)

303-1C6, MH259718/MH259743 (respective CDRs 1-3):

GFLFYSYA, (SEQ ID NO: 71)

ISGNGENT, (SEQ ID NO: 48)

ARDRDWNYFDN/ (SEQ ID NO: 72)

SSNIGSNA, (SEQ ID NO: 50)

VNHQ, (SEQ ID NO: 51)

AAWDDRLNGYV. (SEQ ID NO: 52)

303-1C9, MH259719/MH259744 (respective CDRs 1-3):

GLNFKTQA, (SEQ ID NO: 73)

ISGGGGNT, (SEQ ID NO: 74)

ANCPGDSDNCYWFDP/ (SEQ ID NO: 75)

QGINRW (SEQ ID NO: 76)

AASS, (SEQ ID NO: 63)

QQAKNFPLT. (SEQ ID NO: 77)

303-1D7, MH259720/MH259745 (respective CDRs 1-3):

GFTFRTVA, (SEQ ID NO: 41)

ISHAGTSK, (SEQ ID NO: 42)

ARDGSFGLDY/ (SEQ ID NO: 43)

QGIRSD, (SEQ ID NO: 44)

GAST, (SEQ ID NO: 45)

LQDYNDPYT. (SEQ ID NO: 46)

303-1E3, MH259721/MH259746 (respective CDRs 1-3):

GGSISSNDYY, (SEQ ID NO: 78)

ISYNGDT, (SEQ ID NO: 79)

ARVRTSSTTSYYFDY/QGIRNY, (SEQ ID NO: 80)

-continued

GASS,

QQSYRTLT.

303-1E8, MH259722/MH259747
(respective CDRs 1-3):

GGSITSGSFY QQSYRTLT, (SEQ ID NO: 81)

IFKTGST, (SEQ ID NO: 82)

ARAPFYNDFSGYSYYFDY/ (SEQ ID NO: 83)

SSDIGPNT, (SEQ ID NO: 84)

SDNQ, (SEQ ID NO: 85)

AAWDDSLNPLYV. (SEQ ID NO: 86)

303-1E12, MH259723/MH259748
(respective CDRs 1-3):

GYTFSAYY, (SEQ ID NO: 87)

INPSSGYT, (SEQ ID NO: 88)

ARWEGGDWFAFDF/ (SEQ ID NO: 89)

KLGDKD, (SEQ ID NO: 90)

QDNK, (SEQ ID NO: 91)

QAWDSSTASFV. (SEQ ID NO: 92)

303-1F5, MH259724/MH259749
(respective CDRs 1-3):

GFNFSDYA, (SEQ ID NO: 93)

VSYDGRYK, (SEQ ID NO: 94)

AKDILTGYYKGNFDY/ (SEQ ID NO: 95)

QILSGE, (SEQ ID NO: 96)

DAST, (SEQ ID NO: 97)

QLRNGWLFT. (SEQ ID NO: 98)

303-1F7, MH259725/MH259750
(respective CDRs 1-3):

GASISSSSNY, (SEQ ID NO: 99)

IYYSGNT, (SEQ ID NO: 100)

ATGALRRPFDS/, (SEQ ID NO: 101)

QGISNY, (SEQ ID NO: 102)

AAST, (SEQ ID NO: 14)

LKCNTAPWT. (SEQ ID NO: 104)

303-1G1, MH2597226/MH259751
(respective CDRs 1-3):

GGSISRGGHY, (SEQ ID NO: 105)

IYYSGRT, (SEQ ID NO: 106)

ARDSGYCSSTNCPQNWFDP/ (SEQ ID NO: 107)

QSINTY, (SEQ ID NO: 108)

AASS, (SEQ ID NO: 63)

QQSYTTPQT. (SEQ ID NO: 109)

304-1A12, MH259727/MH259752
(respective CDRs 1-3):

GFSGSTHW, (SEQ ID NO: 110)

IKPDGSEK, (SEQ ID NO: 111)

ARSPRFLSQDYYYYVMDV/ (SEQ ID NO: 112)

HSISTY, (SEQ ID NO: 113)

AAST, (SEQ ID NO: 14)

QQSFITRTWT. (SEQ ID NO: 114)

RM-1A2, MH259728/MH259753
(respective CDRs 1-3):

GYVFNEYY, (SEQ ID NO: 115)

INPNSGDA, (SEQ ID NO: 116)

ARIMYFEYDSWSDY/ (SEQ ID NO: 117)

QSIRSN, (SEQ ID NO: 118)

ATSS, (SEQ ID NO: 119)

QQSYSLPWT. (SEQ ID NO: 120)

RM-1D1, MH259729/MH259754 (respective CDRs 1-3):

GFAFSDYY, (SEQ ID NO: 121)

ISGSGTTI, (SEQ ID NO: 122)

AREPPYTSSIDY/ (SEQ ID NO: 123)

QNIRTY, (SEQ ID NO: 124)

(SEQ ID NO: 125)
SASS, (SEQ ID NO: 126)
QQSYSTPWT.

RM-5A2, MH259731/MH259756 (respective CDRs 1-3):
(SEQ ID NO: 127)
GGSISRYY, (SEQ ID NO: 128)
IYYTGTT, (SEQ ID NO: 129)
ARIGGVSFGERPIDY/

(SEQ ID NO: 130)
QTISTY, (SEQ ID NO: 14)
AAST, (SEQ ID NO: 131)
QQSYSIPLT.

RM-5B3, MH259732/MH259757 (respective CDRs 1-3):
(SEQ ID NO: 132)
GYRFSSQW, (SEQ ID NO: 133)
IFPGDSDV, (SEQ ID NO: 134)
ARQRYSSGSFGY/

(SEQ ID NO: 135)
QSVLYTPNNKNY, (SEQ ID NO: 21)
WAST, (SEQ ID NO: 136)
QQYETYPFT.

---

What is claimed is:

1. A recombinant chimeric antibody or fragment comprising six complementarity determining regions (CDRs) of antibody RM-2D6, wherein the CDRs comprise three heavy chain CDRs, wherein heavy chain CDR 1 comprises the amino acid sequence of GFMFSSYG (SEQ ID NO: 3); CDR 2 comprises the amino acid sequence of VSHDGTND (SEQ ID NO: 4), and CDR 3 comprises the amino acid sequence of AKTSWARFLEWTFDY (SEQ ID NO: 1), and, wherein the CDRs comprise three light chain CDRs, wherein light chain CDR 1 comprises the amino acid sequence of QSINRY (SEQ ID NO: 5); light chain CDR2 comprises the amino acid sequence of GASS (SEQ ID NO: 6); and light chain CDR3 comprises the amino acid sequence of QQSHSTPT (SEQ ID NO: 2); and, wherein the antibody or fragment specifically binds a glycoprotein of varicella-zoster virus.

2. The antibody of claim 1, wherein the heavy chain variable region comprises EVQLVES-GGGVVQPGRSLRLS-CAASGFMFSSYGMHWVRQAPGK-GLEWVAAVSHDGT NDLYADSVKGRFSISRDNSKNTLYLQMNSLRAED-TAVYYCAKTSWARFLEWTFDYWG QGTLVTVSS (SEQ ID NO: 7).

3. The antibody of claim 1, wherein the light chain variable region comprises DIQMTQSPSSL-SASVGDRVTITCRASQSIN-RYLNWYQQKPGKAPKLLIYGASSLQSGVPL

RFSGSGSGTDFTLTISSLQPEDFATYYCQQSH-STP

SEQUENCE LISTING

```
<160> NUMBER OF SEQ ID NOS: 137

<210> SEQ ID NO 1
<211> LENGTH: 15
<212> TYPE: PRT
<213> ORGANISM: Artificial
<220> FEATURE:
<223> OTHER INFORMATION: Synthetic construct

<400> SEQUENCE: 1

Ala Lys Thr Ser Trp Ala Arg Phe Leu Glu Trp Thr Phe Asp Tyr
1               5                   10                  15

<210> SEQ ID NO 2
<211> LENGTH: 8
<212> TYPE: PRT
<213> ORGANISM: Artificial
<220> FEATURE:
<223> OTHER INFORMATION: Synthetic construct

<400> SEQUENCE: 2

Gln Gln Ser His Ser Thr Pro Thr
1               5

<210> SEQ ID NO 3
<211> LENGTH: 8
<212> TYPE: PRT
<213> ORGANISM: Artificial
<220> FEATURE:
<223> OTHER INFORMATION: Synthetic construct

<400> SEQUENCE: 3

Gly Phe Met Phe Ser Ser Tyr Gly
1               5

<210> SEQ ID NO 4
<211> LENGTH: 8
<212> TYPE: PRT
<213> ORGANISM: Artificial
<220> FEATURE:
<223> OTHER INFORMATION: Synthetic construct

<400> SEQUENCE: 4

Val Ser His Asp Gly Thr Asn Asp
1               5
```

```
<210> SEQ ID NO 5
<211> LENGTH: 6
<212> TYPE: PRT
<213> ORGANISM: Artificial
<220> FEATURE:
<223> OTHER INFORMATION: Synthetic construct

<400> SEQUENCE: 5

Gln Ser Ile Asn Arg Tyr
1               5

<210> SEQ ID NO 6
<211> LENGTH: 4
<212> TYPE: PRT
<213> ORGANISM: Artificial
<220> FEATURE:
<223> OTHER INFORMATION: Synthetic construct

<400> SEQUENCE: 6

Gly Ala Ser Ser
1

<210> SEQ ID NO 7
<211> LENGTH: 122
<212> TYPE: PRT
<213> ORGANISM: Artificial
<220> FEATURE:
<223> OTHER INFORMATION: Synthetic construct

<400> SEQUENCE: 7

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Met Phe Ser Ser Tyr
            20                  25                  30

Gly Met His Trp Val Arg Gln Ala Pro Gly Lys Gly Leu Glu Trp Val
        35                  40                  45

Ala Ala Val Ser His Asp Gly Thr Asn Asp Leu Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Trp Ala Arg Phe Leu Glu Trp Thr Phe Asp Tyr Trp
            100                 105                 110

Gly Gln Gly Thr Leu Val Thr Val Ser Ser
        115                 120

<210> SEQ ID NO 8
<211> LENGTH: 106
<212> TYPE: PRT
<213> ORGANISM: Artificial
<220> FEATURE:
<223> OTHER INFORMATION: Synthetic construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Arg Tyr
            20                  25                  30

Leu Asn Trp Tyr Gln Gln Lys Pro Gly Lys Ala Pro Lys Leu Leu Ile
        35                  40                  45
```

```
Tyr Gly Ala Ser Ser Leu Gln Ser Gly Val Pro Leu Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser His Ser Thr Pro Thr
                85                  90                  95
Phe Gly Gln Gly Thr Arg Leu Glu Ile Lys
            100                 105
```

<210> SEQ ID NO 9
<211> LENGTH: 16
<212> TYPE: PRT
<213> ORGANISM: Artificial
<220> FEATURE:
<223> OTHER INFORMATION: Synthetic construct

<400> SEQUENCE: 9

```
Ala Arg Asp Arg Gly Gly Ser Leu Ala Met Val Val Gly Leu Asp His
1               5                   10                  15
```

<210> SEQ ID NO 10
<211> LENGTH: 9
<212> TYPE: PRT
<213> ORGANISM: Artificial
<220> FEATURE:
<223> OTHER INFORMATION: Synthetic construct

<400> SEQUENCE: 10

```
Gln Gln Cys Tyr Ser Ala Glu Leu Thr
1               5
```

<210> SEQ ID NO 11
<211> LENGTH: 8
<212> TYPE: PRT
<213> ORGANISM: Artificial
<220> FEATURE:
<223> OTHER INFORMATION: Synthetic construct

<400> SEQUENCE: 11

```
Gly Tyr Thr Phe Ser Asn Tyr Gly
1               5
```

<210> SEQ ID NO 12
<211> LENGTH: 8
<212> TYPE: PRT
<213> ORGANISM: Artificial
<220> FEATURE:
<223> OTHER INFORMATION: Synthetic construct

<400> SEQUENCE: 12

```
Ile Ser Ala Ser Asn Ala Asn Thr
1               5
```

<210> SEQ ID NO 13
<211> LENGTH: 6
<212> TYPE: PRT
<213> ORGANISM: Artificial
<220> FEATURE:
<223> OTHER INFORMATION: Synthetic construct

<400> SEQUENCE: 13

```
Gln Ser Ile Gly Gly Tyr
1               5
```

```
<210> SEQ ID NO 14
<211> LENGTH: 4
<212> TYPE: PRT
<213> ORGANISM: Artificial
<220> FEATURE:
<223> OTHER INFORMATION: Synthetic construct

<400> SEQUENCE: 14

Ala Ala Ser Thr
1

<210> SEQ ID NO 15
<211> LENGTH: 123
<212> TYPE: PRT
<213> ORGANISM: Artificial
<220> FEATURE:
<223> OTHER INFORMATION: Synthetic construct

<400> SEQUENCE: 15

Gln Val Gln Leu Val Gln Ser Gly Ala Glu Val Lys Lys Pro Gly Ala
1               5                   10                  15

Ser Val Lys Val Ser Cys Glu Ala Phe Gly Tyr Thr Phe Ser Asn Tyr
            20                  25                  30

Gly Phe Thr Trp Val Arg Gln Ala Pro Gly Gln Gly Leu Glu Trp Met
        35                  40                  45

Gly Trp Ile Ser Ala Ser Asn Ala Asn Thr Lys Tyr Gly Gln Lys Phe
    50                  55                  60

Arg Gly Arg Val Thr Leu Thr Thr Asp Thr Ser Thr Ser Thr Ala Tyr
65                  70                  75                  80

Met Glu Leu Arg Asn Leu Gly Tyr Asp Asp Thr Ala Met Tyr Tyr Cys
                85                  90                  95

Ala Arg Asp Arg Gly Gly Ser Leu Ala Met Val Val Gly Leu Asp His
            100                 105                 110

Trp Gly Gln Gly Thr Leu Val Thr Val Ser Ser
        115                 120

<210> SEQ ID NO 16
<211> LENGTH: 107
<212> TYPE: PRT
<213> ORGANISM: Artificial
<220> FEATURE:
<223> OTHER INFORMATION: Synthetic construct

<400> SEQUENCE: 16

Asp Ile Gln Met Thr Gln Ser Pro Thr Ser Leu Ser Ala Ser Val Gly
1               5                   10                  15

Asp Arg Val Thr Ile Thr Cys Arg Ala Ser Gln Ser Ile Gly Gly Tyr
            20                  25                  30

Leu Asn Trp Tyr Gln Gln Asn Pro Gly Lys Ala Pro Lys Leu Leu Ile
        35                  40                  45

Tyr Ala Ala Ser Thr Leu Gln Arg Gly Val Pro Ser Arg Phe Ser Gly
    50                  55                  60

Gly Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Cys Tyr Ser Ala Glu Leu
                85                  90                  95

Thr Phe Gly Gly Gly Thr Lys Val Glu Ile Lys
            100                 105

<210> SEQ ID NO 17
```

```
<211> LENGTH: 8
<212> TYPE: PRT
<213> ORGANISM: Artificial
<220> FEATURE:
<223> OTHER INFORMATION: Synthetic construct

<400> SEQUENCE: 17

Gly Tyr Arg Phe Thr Gly Tyr Tyr
1               5

<210> SEQ ID NO 18
<211> LENGTH: 8
<212> TYPE: PRT
<213> ORGANISM: Artificial
<220> FEATURE:
<223> OTHER INFORMATION: Synthetic construct

<400> SEQUENCE: 18

Val Asn Pro Gln Ser Gly Gly Thr
1               5

<210> SEQ ID NO 19
<211> LENGTH: 15
<212> TYPE: PRT
<213> ORGANISM: Artificial
<220> FEATURE:
<223> OTHER INFORMATION: Synthetic construct

<400> SEQUENCE: 19

Ala Thr Leu Thr Arg Glu Thr Gly Ala Pro Ser Thr Phe Asp Tyr
1               5                   10                  15

<210> SEQ ID NO 20
<211> LENGTH: 12
<212> TYPE: PRT
<213> ORGANISM: Artificial
<220> FEATURE:
<223> OTHER INFORMATION: Synthetic construct

<400> SEQUENCE: 20

His Ser Val Leu Asn Ser Ala Asn Asn Lys Asn Tyr
1               5                   10

<210> SEQ ID NO 21
<211> LENGTH: 4
<212> TYPE: PRT
<213> ORGANISM: Artificial
<220> FEATURE:
<223> OTHER INFORMATION: Synthetic construct

<400> SEQUENCE: 21

Trp Ala Ser Thr
1

<210> SEQ ID NO 22
<211> LENGTH: 9
<212> TYPE: PRT
<213> ORGANISM: Artificial
<220> FEATURE:
<223> OTHER INFORMATION: Synthetic construct

<400> SEQUENCE: 22

Gln His Tyr Tyr Asn Thr Pro Leu Thr
1               5

<210> SEQ ID NO 23
<211> LENGTH: 8
```

```
<212> TYPE: PRT
<213> ORGANISM: Artificial
<220> FEATURE:
<223> OTHER INFORMATION: Synthetic construct

<400> SEQUENCE: 23

Gly Gly Thr Phe Gly Ser His Ala
1               5

<210> SEQ ID NO 24
<211> LENGTH: 8
<212> TYPE: PRT
<213> ORGANISM: Artificial
<220> FEATURE:
<223> OTHER INFORMATION: Synthetic construct

<400> SEQUENCE: 24

Ile Ile Pro Ile Leu Ala Leu Val
1               5

<210> SEQ ID NO 25
<211> LENGTH: 15
<212> TYPE: PRT
<213> ORGANISM: Artificial
<220> FEATURE:
<223> OTHER INFORMATION: Synthetic construct

<400> SEQUENCE: 25

Ala Arg Gly Gly Ser Phe Ser Leu Gly Ala Asn Gly Leu Asp Val
1               5                   10                  15

<210> SEQ ID NO 26
<211> LENGTH: 7
<212> TYPE: PRT
<213> ORGANISM: Artificial
<220> FEATURE:
<223> OTHER INFORMATION: Synthetic construct

<400> SEQUENCE: 26

Gln Ser Val Ser Ser Thr Tyr
1               5

<210> SEQ ID NO 27
<211> LENGTH: 4
<212> TYPE: PRT
<213> ORGANISM: Artificial
<220> FEATURE:
<223> OTHER INFORMATION: Synthetic construct

<400> SEQUENCE: 27

Gly Ala Ser Arg
1

<210> SEQ ID NO 28
<211> LENGTH: 9
<212> TYPE: PRT
<213> ORGANISM: Artificial
<220> FEATURE:
<223> OTHER INFORMATION: Synthetic construct

<400> SEQUENCE: 28

Gln Gln His Gly Ser Leu Pro Trp Thr
1               5

<210> SEQ ID NO 29
<211> LENGTH: 8
<212> TYPE: PRT
```

<213> ORGANISM: Artificial
<220> FEATURE:
<223> OTHER INFORMATION: Synthetic construct

<400> SEQUENCE: 29

Gly Gly Thr Phe Ser Ser Tyr Val
1               5

<210> SEQ ID NO 30
<211> LENGTH: 8
<212> TYPE: PRT
<213> ORGANISM: Artificial
<220> FEATURE:
<223> OTHER INFORMATION: Synthetic construct

<400> SEQUENCE: 30

Ile Ile Pro Met Leu Gly Val Ser
1               5

<210> SEQ ID NO 31
<211> LENGTH: 16
<212> TYPE: PRT
<213> ORGANISM: Artificial
<220> FEATURE:
<223> OTHER INFORMATION: Synthetic construct

<400> SEQUENCE: 31

Ala Ile Arg Gly Gly Met Thr Thr Leu Thr Pro Glu Asp Leu Asp Val
1               5                   10                  15

<210> SEQ ID NO 32
<211> LENGTH: 11
<212> TYPE: PRT
<213> ORGANISM: Artificial
<220> FEATURE:
<223> OTHER INFORMATION: Synthetic construct

<400> SEQUENCE: 32

Gln Ser Leu Leu His Ser Asp Gly Lys Thr Tyr
1               5                   10

<210> SEQ ID NO 33
<211> LENGTH: 4
<212> TYPE: PRT
<213> ORGANISM: Artificial
<220> FEATURE:
<223> OTHER INFORMATION: Synthetic construct

<400> SEQUENCE: 33

Gln Val Ser Lys
1

<210> SEQ ID NO 34
<211> LENGTH: 9
<212> TYPE: PRT
<213> ORGANISM: Artificial
<220> FEATURE:
<223> OTHER INFORMATION: Synthetic construct

<400> SEQUENCE: 34

Met Gln Ser Ile His Leu Pro Leu Thr
1               5

<210> SEQ ID NO 35
<211> LENGTH: 8
<212> TYPE: PRT
<213> ORGANISM: Artificial

<220> FEATURE:
<223> OTHER INFORMATION: Synthetic construct

<400> SEQUENCE: 35

Gly Phe Asn Phe His Glu Tyr Gly
1               5

<210> SEQ ID NO 36
<211> LENGTH: 8
<212> TYPE: PRT
<213> ORGANISM: Artificial
<220> FEATURE:
<223> OTHER INFORMATION: Synthetic construct

<400> SEQUENCE: 36

Ile Asn Trp Asn Ser Gly Thr Ile
1               5

<210> SEQ ID NO 37
<211> LENGTH: 22
<212> TYPE: PRT
<213> ORGANISM: Artificial
<220> FEATURE:
<223> OTHER INFORMATION: Synthetic construct

<400> SEQUENCE: 37

Ala Lys Asp Gln Tyr Cys Gly Gly Asp Cys His Ser Lys Ser Tyr Tyr
1               5                   10                  15

Tyr Tyr Gly Met Asp Val
            20

<210> SEQ ID NO 38
<211> LENGTH: 8
<212> TYPE: PRT
<213> ORGANISM: Artificial
<220> FEATURE:
<223> OTHER INFORMATION: Synthetic construct

<400> SEQUENCE: 38

Ser Gly Ser Ile Ala Ser Asn Tyr
1               5

<210> SEQ ID NO 39
<211> LENGTH: 4
<212> TYPE: PRT
<213> ORGANISM: Artificial
<220> FEATURE:
<223> OTHER INFORMATION: Synthetic construct

<400> SEQUENCE: 39

Glu Asp Asn Gln
1

<210> SEQ ID NO 40
<211> LENGTH: 10
<212> TYPE: PRT
<213> ORGANISM: Artificial
<220> FEATURE:
<223> OTHER INFORMATION: Synthetic construct

<400> SEQUENCE: 40

Gln Ser Tyr Asp Ser Gln Thr Ala Val Ile
1               5                   10

<210> SEQ ID NO 41
<211> LENGTH: 8

```
<212> TYPE: PRT
<213> ORGANISM: Artificial
<220> FEATURE:
<223> OTHER INFORMATION: Synthetic construct

<400> SEQUENCE: 41

Gly Phe Thr Phe Arg Thr Val Ala
1               5

<210> SEQ ID NO 42
<211> LENGTH: 8
<212> TYPE: PRT
<213> ORGANISM: Artificial
<220> FEATURE:
<223> OTHER INFORMATION: Synthetic construct

<400> SEQUENCE: 42

Ile Ser His Ala Gly Thr Ser Lys
1               5

<210> SEQ ID NO 43
<211> LENGTH: 10
<212> TYPE: PRT
<213> ORGANISM: Artificial
<220> FEATURE:
<223> OTHER INFORMATION: Synthetic construct

<400> SEQUENCE: 43

Ala Arg Asp Gly Ser Phe Gly Leu Asp Tyr
1               5                   10

<210> SEQ ID NO 44
<211> LENGTH: 6
<212> TYPE: PRT
<213> ORGANISM: Artificial
<220> FEATURE:
<223> OTHER INFORMATION: Synthetic construct

<400> SEQUENCE: 44

Gln Gly Ile Arg Ser Asp
1               5

<210> SEQ ID NO 45
<211> LENGTH: 4
<212> TYPE: PRT
<213> ORGANISM: Artificial
<220> FEATURE:
<223> OTHER INFORMATION: Synthetic construct

<400> SEQUENCE: 45

Gly Ala Ser Thr
1

<210> SEQ ID NO 46
<211> LENGTH: 9
<212> TYPE: PRT
<213> ORGANISM: Artificial
<220> FEATURE:
<223> OTHER INFORMATION: Synthetic construct

<400> SEQUENCE: 46

Leu Gln Asp Tyr Asn Asp Pro Tyr Thr
1               5

<210> SEQ ID NO 47
<211> LENGTH: 8
<212> TYPE: PRT
```

<213> ORGANISM: Artificial
<220> FEATURE:
<223> OTHER INFORMATION: Synthetic construct

<400> SEQUENCE: 47

Gly Phe Leu Phe Tyr Ser Tyr Gly
1               5

<210> SEQ ID NO 48
<211> LENGTH: 8
<212> TYPE: PRT
<213> ORGANISM: Artificial
<220> FEATURE:
<223> OTHER INFORMATION: Synthetic construct

<400> SEQUENCE: 48

Ile Ser Gly Asn Gly Glu Asn Thr
1               5

<210> SEQ ID NO 49
<211> LENGTH: 11
<212> TYPE: PRT
<213> ORGANISM: Artificial
<220> FEATURE:
<223> OTHER INFORMATION: Synthetic construct

<400> SEQUENCE: 49

Ala Arg Asp Arg Asp Trp Asn Tyr Phe Asp Lys
1               5                   10

<210> SEQ ID NO 50
<211> LENGTH: 8
<212> TYPE: PRT
<213> ORGANISM: Artificial
<220> FEATURE:
<223> OTHER INFORMATION: Synthetic construct

<400> SEQUENCE: 50

Ser Ser Asn Ile Gly Ser Asn Ala
1               5

<210> SEQ ID NO 51
<211> LENGTH: 4
<212> TYPE: PRT
<213> ORGANISM: Artificial
<220> FEATURE:
<223> OTHER INFORMATION: Synthetic construct

<400> SEQUENCE: 51

Val Asn His Gln
1

<210> SEQ ID NO 52
<211> LENGTH: 11
<212> TYPE: PRT
<213> ORGANISM: Artificial
<220> FEATURE:
<223> OTHER INFORMATION: Synthetic construct

<400> SEQUENCE: 52

Ala Ala Trp Asp Asp Arg Leu Asn Gly Tyr Val
1               5                   10

<210> SEQ ID NO 53
<211> LENGTH: 10
<212> TYPE: PRT
<213> ORGANISM: Artificial

```
<220> FEATURE:
<223> OTHER INFORMATION: Synthetic construct

<400> SEQUENCE: 53

Gly Gly Ser Ile Asn Ser Gly Asp Phe Tyr
1               5                   10

<210> SEQ ID NO 54
<211> LENGTH: 7
<212> TYPE: PRT
<213> ORGANISM: Artificial
<220> FEATURE:
<223> OTHER INFORMATION: Synthetic construct

<400> SEQUENCE: 54

Ile Tyr His Gly Gly Gly Thr
1               5

<210> SEQ ID NO 55
<211> LENGTH: 15
<212> TYPE: PRT
<213> ORGANISM: Artificial
<220> FEATURE:
<223> OTHER INFORMATION: Synthetic construct

<400> SEQUENCE: 55

Ala Arg Glu Ser Ile Gly Asp Asp Phe Trp Ser Gly Leu Gly Pro
1               5                   10                  15

<210> SEQ ID NO 56
<211> LENGTH: 11
<212> TYPE: PRT
<213> ORGANISM: Artificial
<220> FEATURE:
<223> OTHER INFORMATION: Synthetic construct

<400> SEQUENCE: 56

Gln Ser Leu Leu His Ser Asn Gly His Asn Phe
1               5                   10

<210> SEQ ID NO 57
<211> LENGTH: 4
<212> TYPE: PRT
<213> ORGANISM: Artificial
<220> FEATURE:
<223> OTHER INFORMATION: Synthetic construct

<400> SEQUENCE: 57

Leu Gly Ser Asn
1

<210> SEQ ID NO 58
<211> LENGTH: 9
<212> TYPE: PRT
<213> ORGANISM: Artificial
<220> FEATURE:
<223> OTHER INFORMATION: Synthetic construct

<400> SEQUENCE: 58

Met Gln Ala Leu Gln Thr Pro Tyr Thr
1               5

<210> SEQ ID NO 59
<211> LENGTH: 8
<212> TYPE: PRT
<213> ORGANISM: Artificial
<220> FEATURE:
```

<223> OTHER INFORMATION: Synthetic construct

<400> SEQUENCE: 59

Gly Ile Ser Val Ser Ser Asn Tyr
1               5

<210> SEQ ID NO 60
<211> LENGTH: 7
<212> TYPE: PRT
<213> ORGANISM: Artificial
<220> FEATURE:
<223> OTHER INFORMATION: Synthetic construct

<400> SEQUENCE: 60

Thr Tyr Ser Gly Gly Ser Thr
1               5

<210> SEQ ID NO 61
<211> LENGTH: 14
<212> TYPE: PRT
<213> ORGANISM: Artificial
<220> FEATURE:
<223> OTHER INFORMATION: Synthetic construct

<400> SEQUENCE: 61

Ala Arg Glu Ala Tyr Asn Ser Gly Thr Tyr Tyr Phe Asp Tyr
1               5                   10

<210> SEQ ID NO 62
<211> LENGTH: 6
<212> TYPE: PRT
<213> ORGANISM: Artificial
<220> FEATURE:
<223> OTHER INFORMATION: Synthetic construct

<400> SEQUENCE: 62

Gln Ser Ile Ser Lys Ser
1               5

<210> SEQ ID NO 63
<211> LENGTH: 4
<212> TYPE: PRT
<213> ORGANISM: Artificial
<220> FEATURE:
<223> OTHER INFORMATION: Synthetic construct

<400> SEQUENCE: 63

Ala Ala Ser Ser
1

<210> SEQ ID NO 64
<211> LENGTH: 9
<212> TYPE: PRT
<213> ORGANISM: Artificial
<220> FEATURE:
<223> OTHER INFORMATION: Synthetic construct

<400> SEQUENCE: 64

Gln Gln Ser His Thr Ile Pro Tyr Thr
1               5

<210> SEQ ID NO 65
<211> LENGTH: 8
<212> TYPE: PRT
<213> ORGANISM: Artificial
<220> FEATURE:
<223> OTHER INFORMATION: Synthetic construct

```
<400> SEQUENCE: 65

Gly Phe Thr Leu Ser Ser His Asp
1               5

<210> SEQ ID NO 66
<211> LENGTH: 8
<212> TYPE: PRT
<213> ORGANISM: Artificial
<220> FEATURE:
<223> OTHER INFORMATION: Synthetic construct

<400> SEQUENCE: 66

Ile Ser Tyr Asp Gly Ser Asn Lys
1               5

<210> SEQ ID NO 67
<211> LENGTH: 14
<212> TYPE: PRT
<213> ORGANISM: Artificial
<220> FEATURE:
<223> OTHER INFORMATION: Synthetic construct

<400> SEQUENCE: 67

Ala Arg Asp Phe Ser Gly Val Thr Thr Ile Ser Leu Asp Ser
1               5                   10

<210> SEQ ID NO 68
<211> LENGTH: 8
<212> TYPE: PRT
<213> ORGANISM: Artificial
<220> FEATURE:
<223> OTHER INFORMATION: Synthetic construct

<400> SEQUENCE: 68

Ser Ser Asn Ile Gly Asn Asn Ala
1               5

<210> SEQ ID NO 69
<211> LENGTH: 4
<212> TYPE: PRT
<213> ORGANISM: Artificial
<220> FEATURE:
<223> OTHER INFORMATION: Synthetic construct

<400> SEQUENCE: 69

Tyr Asp Asp Lys
1

<210> SEQ ID NO 70
<211> LENGTH: 11
<212> TYPE: PRT
<213> ORGANISM: Artificial
<220> FEATURE:
<223> OTHER INFORMATION: Synthetic construct

<400> SEQUENCE: 70

Ala Ala Trp Asp Asp Ser Leu Asn Arg Gly Val
1               5                   10

<210> SEQ ID NO 71
<211> LENGTH: 8
<212> TYPE: PRT
<213> ORGANISM: Artificial
<220> FEATURE:
<223> OTHER INFORMATION: Synthetic construct
```

```
<400> SEQUENCE: 71

Gly Phe Leu Phe Tyr Ser Tyr Ala
1               5

<210> SEQ ID NO 72
<211> LENGTH: 11
<212> TYPE: PRT
<213> ORGANISM: Artificial
<220> FEATURE:
<223> OTHER INFORMATION: Synthetic construct

<400> SEQUENCE: 72

Ala Arg Asp Arg Asp Trp Asn Tyr Phe Asp Asn
1               5                   10

<210> SEQ ID NO 73
<211> LENGTH: 8
<212> TYPE: PRT
<213> ORGANISM: Artificial
<220> FEATURE:
<223> OTHER INFORMATION: Synthetic construct

<400> SEQUENCE: 73

Gly Leu Asn Phe Lys Thr Gln Ala
1               5

<210> SEQ ID NO 74
<211> LENGTH: 8
<212> TYPE: PRT
<213> ORGANISM: Artificial
<220> FEATURE:
<223> OTHER INFORMATION: Synthetic construct

<400> SEQUENCE: 74

Ile Ser Gly Gly Gly Gly Asn Thr
1               5

<210> SEQ ID NO 75
<211> LENGTH: 15
<212> TYPE: PRT
<213> ORGANISM: Artificial
<220> FEATURE:
<223> OTHER INFORMATION: Synthetic construct

<400> SEQUENCE: 75

Ala Asn Cys Pro Gly Asp Ser Asp Asn Cys Tyr Trp Phe Asp Pro
1               5                   10                  15

<210> SEQ ID NO 76
<211> LENGTH: 6
<212> TYPE: PRT
<213> ORGANISM: Artificial
<220> FEATURE:
<223> OTHER INFORMATION: Synthetic construct

<400> SEQUENCE: 76

Gln Gly Ile Asn Arg Trp
1               5

<210> SEQ ID NO 77
<211> LENGTH: 9
<212> TYPE: PRT
<213> ORGANISM: Artificial
<220> FEATURE:
<223> OTHER INFORMATION: Synthetic construct

<400> SEQUENCE: 77
```

Gln Gln Ala Lys Asn Phe Pro Leu Thr
1               5

<210> SEQ ID NO 78
<211> LENGTH: 10
<212> TYPE: PRT
<213> ORGANISM: Artificial
<220> FEATURE:
<223> OTHER INFORMATION: Synthetic construct

<400> SEQUENCE: 78

Gly Gly Ser Ile Ser Ser Asn Asp Tyr Tyr
1               5                   10

<210> SEQ ID NO 79
<211> LENGTH: 7
<212> TYPE: PRT
<213> ORGANISM: Artificial
<220> FEATURE:
<223> OTHER INFORMATION: Synthetic construct

<400> SEQUENCE: 79

Ile Ser Tyr Asn Gly Asp Thr
1               5

<210> SEQ ID NO 80
<211> LENGTH: 15
<212> TYPE: PRT
<213> ORGANISM: Artificial
<220> FEATURE:
<223> OTHER INFORMATION: Synthetic construct

<400> SEQUENCE: 80

Ala Arg Val Arg Thr Ser Ser Thr Thr Ser Tyr Tyr Phe Asp Tyr
1               5                   10                  15

<210> SEQ ID NO 81
<211> LENGTH: 8
<212> TYPE: PRT
<213> ORGANISM: Artificial
<220> FEATURE:
<223> OTHER INFORMATION: Synthetic construct

<400> SEQUENCE: 81

Gln Gln Ser Tyr Arg Thr Leu Thr
1               5

<210> SEQ ID NO 82
<211> LENGTH: 10
<212> TYPE: PRT
<213> ORGANISM: Artificial
<220> FEATURE:
<223> OTHER INFORMATION: Synthetic construct

<400> SEQUENCE: 82

Gly Gly Ser Ile Thr Ser Gly Ser Phe Tyr
1               5                   10

<210> SEQ ID NO 83
<211> LENGTH: 7
<212> TYPE: PRT
<213> ORGANISM: Artificial
<220> FEATURE:
<223> OTHER INFORMATION: Synthetic construct

<400> SEQUENCE: 83

```
Ile Phe Lys Thr Gly Ser Thr
1               5
```

<210> SEQ ID NO 84
<211> LENGTH: 18
<212> TYPE: PRT
<213> ORGANISM: Artificial
<220> FEATURE:
<223> OTHER INFORMATION: Synthetic construct

<400> SEQUENCE: 84

```
Ala Arg Ala Pro Phe Tyr Asn Asp Phe Ser Gly Tyr Ser Tyr Tyr Phe
1               5                   10                  15
Asp Tyr
```

<210> SEQ ID NO 85
<211> LENGTH: 8
<212> TYPE: PRT
<213> ORGANISM: Artificial
<220> FEATURE:
<223> OTHER INFORMATION: Synthetic construct

<400> SEQUENCE: 85

```
Ser Ser Asp Ile Gly Pro Asn Thr
1               5
```

<210> SEQ ID NO 86
<211> LENGTH: 4
<212> TYPE: PRT
<213> ORGANISM: Artificial
<220> FEATURE:
<223> OTHER INFORMATION: Synthetic construct

<400> SEQUENCE: 86

```
Ser Asp Asn Gln
1
```

<210> SEQ ID NO 87
<211> LENGTH: 12
<212> TYPE: PRT
<213> ORGANISM: Artificial
<220> FEATURE:
<223> OTHER INFORMATION: Synthetic construct

<400> SEQUENCE: 87

```
Ala Ala Trp Asp Asp Ser Leu Asn Pro Leu Tyr Val
1               5                   10
```

<210> SEQ ID NO 88
<211> LENGTH: 8
<212> TYPE: PRT
<213> ORGANISM: Artificial
<220> FEATURE:
<223> OTHER INFORMATION: Synthetic construct

<400> SEQUENCE: 88

```
Gly Tyr Thr Phe Ser Ala Tyr Tyr
1               5
```

<210> SEQ ID NO 89
<211> LENGTH: 8
<212> TYPE: PRT
<213> ORGANISM: Artificial
<220> FEATURE:
<223> OTHER INFORMATION: Synthetic construct

<400> SEQUENCE: 89

```
Ile Asn Pro Ser Ser Gly Tyr Thr
1               5
```

<210> SEQ ID NO 90
<211> LENGTH: 13
<212> TYPE: PRT
<213> ORGANISM: Artificial
<220> FEATURE:
<223> OTHER INFORMATION: Synthetic construct

<400> SEQUENCE: 90

```
Ala Arg Trp Glu Gly Gly Asp Trp Phe Ala Phe Asp Phe
1               5                   10
```

<210> SEQ ID NO 91
<211> LENGTH: 6
<212> TYPE: PRT
<213> ORGANISM: Artificial
<220> FEATURE:
<223> OTHER INFORMATION: Synthetic construct

<400> SEQUENCE: 91

```
Lys Leu Gly Asp Lys Asp
1               5
```

<210> SEQ ID NO 92
<211> LENGTH: 4
<212> TYPE: PRT
<213> ORGANISM: Artificial
<220> FEATURE:
<223> OTHER INFORMATION: Synthetic construct

<400> SEQUENCE: 92

```
Gln Asp Asn Lys
1
```

<210> SEQ ID NO 93
<211> LENGTH: 11
<212> TYPE: PRT
<213> ORGANISM: Artificial
<220> FEATURE:
<223> OTHER INFORMATION: Synthetic construct

<400> SEQUENCE: 93

```
Gln Ala Trp Asp Ser Ser Thr Ala Ser Phe Val
1               5                   10
```

<210> SEQ ID NO 94
<211> LENGTH: 8
<212> TYPE: PRT
<213> ORGANISM: Artificial
<220> FEATURE:
<223> OTHER INFORMATION: Synthetic construct

<400> SEQUENCE: 94

```
Gly Phe Asn Phe Ser Asp Tyr Ala
1               5
```

<210> SEQ ID NO 95
<211> LENGTH: 8
<212> TYPE: PRT
<213> ORGANISM: Artificial
<220> FEATURE:
<223> OTHER INFORMATION: Synthetic construct

<400> SEQUENCE: 95

Val Ser Tyr Asp Gly Arg Tyr Lys
1               5

<210> SEQ ID NO 96
<211> LENGTH: 15
<212> TYPE: PRT
<213> ORGANISM: Artificial
<220> FEATURE:
<223> OTHER INFORMATION: Synthetic construct

<400> SEQUENCE: 96

Ala Lys Asp Ile Leu Thr Gly Tyr Tyr Lys Gly Asn Phe Asp Tyr
1               5                   10                  15

<210> SEQ ID NO 97
<211> LENGTH: 6
<212> TYPE: PRT
<213> ORGANISM: Artificial
<220> FEATURE:
<223> OTHER INFORMATION: Synthetic construct

<400> SEQUENCE: 97

Gln Ile Leu Ser Gly Glu
1               5

<210> SEQ ID NO 98
<211> LENGTH: 4
<212> TYPE: PRT
<213> ORGANISM: Artificial
<220> FEATURE:
<223> OTHER INFORMATION: Synthetic construct

<400> SEQUENCE: 98

Asp Ala Ser Thr
1

<210> SEQ ID NO 99
<211> LENGTH: 9
<212> TYPE: PRT
<213> ORGANISM: Artificial
<220> FEATURE:
<223> OTHER INFORMATION: Synthetic construct

<400> SEQUENCE: 99

Gln Leu Arg Asn Gly Trp Leu Phe Thr
1               5

<210> SEQ ID NO 100
<211> LENGTH: 10
<212> TYPE: PRT
<213> ORGANISM: Artificial
<220> FEATURE:
<223> OTHER INFORMATION: Synthetic construct

<400> SEQUENCE: 100

Gly Ala Ser Ile Ser Ser Ser Ser Asn Tyr
1               5                   10

<210> SEQ ID NO 101
<211> LENGTH: 7
<212> TYPE: PRT
<213> ORGANISM: Artificial
<220> FEATURE:
<223> OTHER INFORMATION: Synthetic construct

<400> SEQUENCE: 101

Ile Tyr Tyr Ser Gly Asn Thr

```
1               5

<210> SEQ ID NO 102
<211> LENGTH: 11
<212> TYPE: PRT
<213> ORGANISM: Artificial
<220> FEATURE:
<223> OTHER INFORMATION: Synthetic construct

<400> SEQUENCE: 102

Ala Thr Gly Ala Leu Arg Arg Pro Phe Asp Ser
1               5                   10

<210> SEQ ID NO 103
<211> LENGTH: 6
<212> TYPE: PRT
<213> ORGANISM: Artificial
<220> FEATURE:
<223> OTHER INFORMATION: Synthetic construct

<400> SEQUENCE: 103

Gln Gly Ile Ser Asn Tyr
1               5

<210> SEQ ID NO 104
<211> LENGTH: 9
<212> TYPE: PRT
<213> ORGANISM: Artificial
<220> FEATURE:
<223> OTHER INFORMATION: Synthetic construct

<400> SEQUENCE: 104

Leu Lys Cys Asn Thr Ala Pro Trp Thr
1               5

<210> SEQ ID NO 105
<211> LENGTH: 10
<212> TYPE: PRT
<213> ORGANISM: Artificial
<220> FEATURE:
<223> OTHER INFORMATION: Synthetic construct

<400> SEQUENCE: 105

Gly Gly Ser Ile Ser Arg Gly Gly His Tyr
1               5                   10

<210> SEQ ID NO 106
<211> LENGTH: 7
<212> TYPE: PRT
<213> ORGANISM: Artificial
<220> FEATURE:
<223> OTHER INFORMATION: Synthetic construct

<400> SEQUENCE: 106

Ile Tyr Tyr Ser Gly Arg Thr
1               5

<210> SEQ ID NO 107
<211> LENGTH: 19
<212> TYPE: PRT
<213> ORGANISM: Artificial
<220> FEATURE:
<223> OTHER INFORMATION: Synthetic construct

<400> SEQUENCE: 107

Ala Arg Asp Ser Gly Tyr Cys Ser Ser Thr Asn Cys Pro Gln Asn Trp
1               5                   10                  15
```

Phe Asp Pro

<210> SEQ ID NO 108
<211> LENGTH: 6
<212> TYPE: PRT
<213> ORGANISM: Artificial
<220> FEATURE:
<223> OTHER INFORMATION: Synthetic construct

<400> SEQUENCE: 108

Gln Ser Ile Asn Thr Tyr
1               5

<210> SEQ ID NO 109
<211> LENGTH: 9
<212> TYPE: PRT
<213> ORGANISM: Artificial
<220> FEATURE:
<223> OTHER INFORMATION: Synthetic construct

<400> SEQUENCE: 109

Gln Gln Ser Tyr Thr Thr Pro Gln Thr
1               5

<210> SEQ ID NO 110
<211> LENGTH: 8
<212> TYPE: PRT
<213> ORGANISM: Artificial
<220> FEATURE:
<223> OTHER INFORMATION: Synthetic construct

<400> SEQUENCE: 110

Gly Phe Ser Phe Ser Thr His Trp
1               5

<210> SEQ ID NO 111
<211> LENGTH: 8
<212> TYPE: PRT
<213> ORGANISM: Artificial
<220> FEATURE:
<223> OTHER INFORMATION: Synthetic construct

<400> SEQUENCE: 111

Ile Lys Pro Asp Gly Ser Glu Lys
1               5

<210> SEQ ID NO 112
<211> LENGTH: 18
<212> TYPE: PRT
<213> ORGANISM: Artificial
<220> FEATURE:
<223> OTHER INFORMATION: Synthetic construct

<400> SEQUENCE: 112

Ala Arg Ser Pro Arg Phe Leu Ser Gln Asp Tyr Tyr Tyr Tyr Val Met
1               5                   10                  15

Asp Val

<210> SEQ ID NO 113
<211> LENGTH: 6
<212> TYPE: PRT
<213> ORGANISM: Artificial
<220> FEATURE:
<223> OTHER INFORMATION: Synthetic construct

<400> SEQUENCE: 113

His Ser Ile Ser Thr Tyr
1               5

<210> SEQ ID NO 114
<211> LENGTH: 10
<212> TYPE: PRT
<213> ORGANISM: Artificial
<220> FEATURE:
<223> OTHER INFORMATION: Synthetic construct

<400> SEQUENCE: 114

Gln Gln Ser Phe Ile Thr Arg Thr Trp Thr
1               5                   10

<210> SEQ ID NO 115
<211> LENGTH: 8
<212> TYPE: PRT
<213> ORGANISM: Artificial
<220> FEATURE:
<223> OTHER INFORMATION: Synthetic construct

<400> SEQUENCE: 115

Gly Tyr Val Phe Asn Glu Tyr Tyr
1               5

<210> SEQ ID NO 116
<211> LENGTH: 8
<212> TYPE: PRT
<213> ORGANISM: Artificial
<220> FEATURE:
<223> OTHER INFORMATION: Synthetic construct

<400> SEQUENCE: 116

Ile Asn Pro Asn Ser Gly Asp Ala
1               5

<210> SEQ ID NO 117
<211> LENGTH: 14
<212> TYPE: PRT
<213> ORGANISM: Artificial
<220> FEATURE:
<223> OTHER INFORMATION: Synthetic construct

<400> SEQUENCE: 117

Ala Arg Ile Met Tyr Phe Glu Tyr Asp Ser Trp Ser Asp Tyr
1               5                   10

<210> SEQ ID NO 118
<211> LENGTH: 6
<212> TYPE: PRT
<213> ORGANISM: Artificial
<220> FEATURE:
<223> OTHER INFORMATION: Synthetic construct

<400> SEQUENCE: 118

Gln Ser Ile Arg Ser Asn
1               5

<210> SEQ ID NO 119
<211> LENGTH: 4
<212> TYPE: PRT
<213> ORGANISM: Artificial
<220> FEATURE:
<223> OTHER INFORMATION: Synthetic construct

<400> SEQUENCE: 119

Ala Thr Ser Ser
1

<210> SEQ ID NO 120
<211> LENGTH: 9
<212> TYPE: PRT
<213> ORGANISM: Artificial
<220> FEATURE:
<223> OTHER INFORMATION: Synthetic construct

<400> SEQUENCE: 120

Gln Gln Ser Tyr Ser Leu Pro Trp Thr
1               5

<210> SEQ ID NO 121
<211> LENGTH: 8
<212> TYPE: PRT
<213> ORGANISM: Artificial
<220> FEATURE:
<223> OTHER INFORMATION: Synthetic construct

<400> SEQUENCE: 121

Gly Phe Ala Phe Ser Asp Tyr Tyr
1               5

<210> SEQ ID NO 122
<211> LENGTH: 8
<212> TYPE: PRT
<213> ORGANISM: Artificial
<220> FEATURE:
<223> OTHER INFORMATION: Synthetic construct

<400> SEQUENCE: 122

Ile Ser Gly Ser Gly Thr Thr Ile
1               5

<210> SEQ ID NO 123
<211> LENGTH: 12
<212> TYPE: PRT
<213> ORGANISM: Artificial
<220> FEATURE:
<223> OTHER INFORMATION: Synthetic construct

<400> SEQUENCE: 123

Ala Arg Glu Pro Pro Tyr Thr Ser Ser Ile Asp Tyr
1               5                   10

<210> SEQ ID NO 124
<211> LENGTH: 6
<212> TYPE: PRT
<213> ORGANISM: Artificial
<220> FEATURE:
<223> OTHER INFORMATION: Synthetic construct

<400> SEQUENCE: 124

Gln Asn Ile Arg Thr Tyr
1               5

<210> SEQ ID NO 125
<211> LENGTH: 4
<212> TYPE: PRT
<213> ORGANISM: Artificial
<220> FEATURE:
<223> OTHER INFORMATION: Synthetic construct

<400> SEQUENCE: 125

Ser Ala Ser Ser

```
<210> SEQ ID NO 126
<211> LENGTH: 9
<212> TYPE: PRT
<213> ORGANISM: Artificial
<220> FEATURE:
<223> OTHER INFORMATION: Synthetic construct

<400> SEQUENCE: 126

Gln Gln Ser Tyr Ser Thr Pro Trp Thr
1               5

<210> SEQ ID NO 127
<211> LENGTH: 8
<212> TYPE: PRT
<213> ORGANISM: Artificial
<220> FEATURE:
<223> OTHER INFORMATION: Synthetic construct

<400> SEQUENCE: 127

Gly Gly Ser Ile Ser Arg Tyr Tyr
1               5

<210> SEQ ID NO 128
<211> LENGTH: 7
<212> TYPE: PRT
<213> ORGANISM: Artificial
<220> FEATURE:
<223> OTHER INFORMATION: Synthetic construct

<400> SEQUENCE: 128

Ile Tyr Tyr Thr Gly Thr Thr
1               5

<210> SEQ ID NO 129
<211> LENGTH: 15
<212> TYPE: PRT
<213> ORGANISM: Artificial
<220> FEATURE:
<223> OTHER INFORMATION: Synthetic construct

<400> SEQUENCE: 129

Ala Arg Ile Gly Gly Val Ser Phe Gly Glu Arg Pro Ile Asp Tyr
1               5                   10                  15

<210> SEQ ID NO 130
<211> LENGTH: 6
<212> TYPE: PRT
<213> ORGANISM: Artificial
<220> FEATURE:
<223> OTHER INFORMATION: Synthetic construct

<400> SEQUENCE: 130

Gln Thr Ile Ser Thr Tyr
1               5

<210> SEQ ID NO 131
<211> LENGTH: 9
<212> TYPE: PRT
<213> ORGANISM: Artificial
<220> FEATURE:
<223> OTHER INFORMATION: Synthetic construct

<400> SEQUENCE: 131

Gln Gln Ser Tyr Ser Ile Pro Leu Thr
1               5
```

<210> SEQ ID NO 132
<211> LENGTH: 8
<212> TYPE: PRT
<213> ORGANISM: Artificial
<220> FEATURE:
<223> OTHER INFORMATION: Synthetic construct

<400> SEQUENCE: 132

Gly Tyr Arg Phe Ser Ser Gln Trp
1               5

<210> SEQ ID NO 133
<211> LENGTH: 8
<212> TYPE: PRT
<213> ORGANISM: Artificial
<220> FEATURE:
<223> OTHER INFORMATION: Synthetic construct

<400> SEQUENCE: 133

Ile Phe Pro Gly Asp Ser Asp Val
1               5

<210> SEQ ID NO 134
<211> LENGTH: 12
<212> TYPE: PRT
<213> ORGANISM: Artificial
<220> FEATURE:
<223> OTHER INFORMATION: Synthetic construct

<400> SEQUENCE: 134

Ala Arg Gln Arg Tyr Ser Ser Gly Ser Phe Gly Tyr
1               5                   10

<210> SEQ ID NO 135
<211> LENGTH: 12
<212> TYPE: PRT
<213> ORGANISM: Artificial
<220> FEATURE:
<223> OTHER INFORMATION: Synthetic construct

<400> SEQUENCE: 135

Gln Ser Val Leu Tyr Thr Pro Asn Asn Lys Asn Tyr
1               5                   10

<210> SEQ ID NO 136
<211> LENGTH: 9
<212> TYPE: PRT
<213> ORGANISM: Artificial
<220> FEATURE:
<223> OTHER INFORMATION: Synthetic construct

<400> SEQUENCE: 136

Gln Gln Tyr Glu Thr Tyr Pro Phe Thr
1               5

<210> SEQ ID NO 137
<211> LENGTH: 328
<212> TYPE: PRT
<213> ORGANISM: Homo sapiens

<400> SEQUENCE: 137

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
                20                  25                  30

```
Pro Glu Pro Val Thr Val Ser Trp Asn Ser Gly Ala Leu Thr Ser Gly
        35                  40                  45
Val His Thr Phe Pro Ala Val Leu Gln Ser Ser Gly Leu Tyr Ser Leu
    50                  55                  60
Ser Ser Val Val Thr Val Pro Ser Ser Ser Leu Gly Thr Gln Thr Tyr
65                  70                  75                  80
Ile Cys Asn Val Asn His Lys Pro Ser Asn Thr Lys Val Asp Lys Lys
                85                  90                  95
Val Glu Pro Lys Ser Cys Asp Lys Thr His Thr Cys Pro Pro Cys Pro
                100                 105                 110
Ala Pro Glu Leu Leu Gly Gly Pro Ser Val Phe Leu Phe Pro Pro Lys
        115                 120                 125
Pro Lys Asp Thr Leu Met Ile Ser Arg Thr Pro Glu Val Thr Cys Val
        130                 135                 140
Val Val Asp Val Ser His Glu Asp Pro Glu Val Lys Phe Asn Trp Tyr
145                 150                 155                 160
Val Asp Gly Val Glu Val His Asn Ala Lys Thr Lys Pro Arg Glu Glu
                165                 170                 175
Gln Tyr Asn Ser Thr Tyr Arg Val Val Ser Val Leu Thr Val Leu His
                180                 185                 190
Gln Asp Trp Leu Asn Gly Lys Glu Tyr Lys Cys Lys Val Ser Asn Lys
        195                 200                 205
Ala Leu Pro Ala Pro Ile Glu Lys Thr Ile Ser Lys Ala Lys Gly Gln
        210                 215                 220
Pro Arg Glu Pro Gln Val Tyr Thr Leu Pro Pro Ser Arg Asp Glu Leu
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
                260                 265                 270
Tyr Lys Thr Thr Pro Pro Val Leu Asp Ser Asp Gly Ser Phe Phe Leu
        275                 280                 285
Tyr Ser Lys Leu Thr Val Asp Lys Ser Arg Trp Gln Gln Gly Asn Val
        290                 295                 300
Phe Ser Cys Ser Val Met His Glu Ala Leu His Asn His Tyr Thr Gln
305                 310                 315                 320
Lys Ser Leu Ser Leu Ser Pro Gly
                325
```